United States Patent [19]

Mueller et al.

[11] Patent Number: 5,346,899
[45] Date of Patent: Sep. 13, 1994

[54] SUBSTITUTED PYRIDINE DERIVATIVES AND PESTICIDES CONTAINING THEM

[75] Inventors: Thomas Mueller, Hessheim; Karl Eicken, Wachenheim; Albrecht Harreus, Ludwigshafen; Hartmann Koenig, Limburgerhof; Costin Rentzea, Heidelberg; Eberhard Ammermann, Heppenheim; Gisela Lorenz, Neustadt, all of Fed. Rep. of Germany

[73] Assignee: BASF Aktiengesellschaft, Ludwigshafen, Fed. Rep. of Germany

[21] Appl. No.: 115,041

[22] Filed: Sep. 1, 1993

[30] Foreign Application Priority Data

Sep. 10, 1992 [DE] Fed. Rep. of Germany ....... 4230215

[51] Int. Cl.$^5$ .................. A01N 43/54; C07D 401/14
[52] U.S. Cl. .................... 514/256; 514/334; 546/257; 544/328; 544/333
[58] Field of Search ............... 546/264, 257; 544/328, 544/333; 514/256, 334

[56] References Cited

U.S. PATENT DOCUMENTS 4,873,248 10/1989 Katoh et al. .................. 514/269

OTHER PUBLICATIONS

Alreja et al. *Heterocycles*, vol. 24, No. 6, pp. 1637–1640, 1986.
Divekar, Can J. Chem. vol. 45, No. 11, pp. 1215–1223, 1967.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

Substituted pyridine compounds of formula I

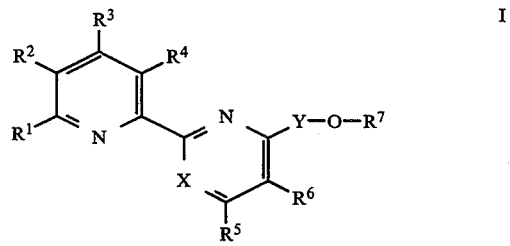

and plant-tolerated acid addition salts and metal salt complexes thereof, and fungicides containing these compounds.

4 Claims, No Drawings

SUBSTITUTED PYRIDINE DERIVATIVES AND PESTICIDES CONTAINING THEM

The present invention relates to novel substituted pyridine derivatives, processes for their preparation, agents containing them and their use as pesticides, in particular as fungicides.

It is known that substituted pyridine derivatives have fungicidal properties (cf. European Patents 270,362, 407,899 and 431,421, Can. J. Microbiol. 5 (1959), 317 and Can. J. Chem. 45 (1967), 1215). However, the activity of these compounds is not always satisfactory, particularly at low application rates and concentrations.

We have found that substituted pyridine derivatives of the formula I

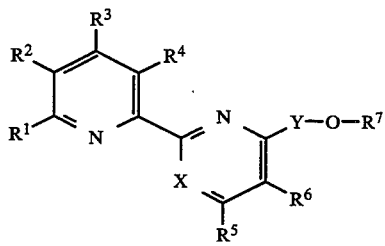

where $R^1$ is hydrogen, $C_1$–$C_6$-alkyl, $C_1$–$C_4$-alkoxy-$C_1$–$C_4$-alkyl, $C_1$–$C_4$-alkylthio-$C_1$–$C_4$-alkyl, $C_2$–$C_6$-alkenyl, $C_2$–$C_6$-alkynyl, $C_3$–$C_7$-cycloalkyl, where the cycloalkyl radical may be monosubstituted, disubstituted or trisubstituted by $C_1$–$C_4$-alkyl, or halogen, phenyl, phenoxy-$C_1$–$C_4$-alkyl, phenylmercapto-$C_1$–$C_4$-alkyl, phenyl-$C_1$–$C_4$-alkyl, phenoxy or phenylmercapto, where the six last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, $R^2$, $R^3$ and $R^4$ independently of one another are each hydrogen, $C_1$–$C_6$-alkyl or phenyl where the phenyl radical may be monosubstituted, disubstituted or trisubstituted by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, $R^5$ is hydrogen, $C_1$–$C_6$-alkyl, $C_3$–$C_7$-cycloalkyl, $C_3$–$C_7$-cycloalkyl-$C_1$–$C_4$-alkyl, where the two last-mentioned radicals may be monosubstituted, disubstituted or trisubstituted in the cycloalkyl moiety by $C_1$–$C_4$-alkyl, or $C_1$–$C_4$-haloalkyl, $C_1$–$C_4$-alkoxy, $C_1$–$C_4$-alkylthio, $C_1$–$C_4$-alkoxy-$C_1$–$C_4$-alkyl, $R^8R^9N$—, $C_1$–$C_4$-alkylthio-$C_1$–$C_4$-alkyl, hydroxyl, halogen, $C_2$–$C_6$-alkenyl, $C_2$–$C_6$-alkynyl, $C_3$–$C_6$-alkenyloxy, $C_3$–$C_6$-alkynyloxy, phenyl, phenoxy, phenyl-$C_1$–$C_4$-alkyl, phenoxy-$C_1$–$C_4$-alkyl, phenylmercapto-$C_1$–$C_4$-alkyl or phenylmercapto, where the six last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, $R^6$ is hydrogen, $C_1$–$C_4$-alkyl, $C_1$–$C_4$-alkoxy, $C_1$–$C_4$-alkoxycarbonyl, halogen or phenyl, where the phenyl radical may be monosubstituted, disubstituted or trisubstituted by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, or $R^5$ and $R^6$ together form a polymethyl-ene chain of the formula —$(CH_2)_m$— in which m is 3 or 4, $R^7$ is hydrogen, $C_1$–$C_{12}$-alkyl, $C_3$–$C_{12}$-alkenyl, $C_3$–$C_8$-alkynyl, where the three last-mentioned groups may be monosubstituted, disubstituted or trisubstituted by halogen, or $C_1$–$C_6$-alkoxy-$C_2$–$C_{10}$-alkyl, monocyclic or polycyclic $C_3$–$C_{10}$-cycloalkyl or $C_3$–$C_{10}$-cycloalkylmethyl, where these rings may be monosubstituted, disubstituted or trisubstituted by $C_1$–$C_4$-alkyl or monosubstituted by phenyl, or monocyclic or polycyclic $C_5$–$C_{10}$-cycloalkenyl or $C_5$–$C_{10}$-cycloalkenylmethyl, where these rings may be monosubstituted, disubstituted or trisubstituted by $C_1$–$C_4$-alkyl or monosubstituted by phenyl, or phenyl or phenyl-$C_1$–$C_6$-alkyl, phenyl-$C_3$–$C_6$-alkenyl or phenoxy-$C_2$–$C_6$-alkyl, where the four last-mentioned radicals may be monosubstituted, disubstituted or trisubstituted in the phenyl moiety by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, $R^8$ and $R^9$ independently of one another are each hydrogen, $C_1$–$C_6$-alkyl, $C_3$–$C_6$-alkenyl, $C_3$–$C_6$-alkynyl, $C_3$–$C_7$-cycloalkyl, where the cycloalkyl radical may be monosubstituted, disubstituted or trisubstituted by $C_1$–$C_4$-alkyl, or phenyl or phenyl-$C_1$–$C_4$-alkyl, where the two last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, or the two radicals $R^8$ and $R^9$, together with the nitrogen atom to which they are bonded, form an unsubstituted or monosubstituted, disubstituted, trisubstituted or tetrasubstituted 5- to 7-membered, saturated or unsaturated heterocyclic structure having 1 to 3 identical or different hetero atoms, preferably nitrogen, oxygen and/or sulfur, and the substituent $C_1$–$C_4$-alkyl, X is CH or N, Y is

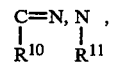

$R^{10}$ is hydrogen or $C_1$–$C_6$-alkyl and $R^{11}$ is hydrogen, $C_1$–$C_6$-alkyl or $C_3$–$C_8$-cycloalkyl, where the cycloalkyl radical may be monosubstituted, disubstituted or trisubstituted by $C_1$–$C_4$-alkyl or monosubstituted by phenyl, or phenyl or phenyl-$C_1$–$C_4$-alkyl, where the two last-mentioned radicals may be monosubstituted, disubstituted or trisubstituted in the phenyl moiety by halogen, $C_1$–$C_4$-alkyl, $C_1$–$C_4$-alkoxy or $C_1$–$C_4$-haloalkyl, and their plant-tolerated acid addition salts and metal salt complexes, with the exception of the compounds E-6-formyloximino-4-methoxy-2,2'-bipyridine, Z-6-formyloximino-4-methoxy-2,2'-bipyridine and 6-formyl-O-methyloximino-4-methoxy-2,2'-bipyridine, have excellent fungicidal activities against phytopathogenic fungi.

If Y is NH or $R^5$ is OH, the compounds may be present in tautomeric forms, to which the present invention relates.

If Y is $CR^{10}$=N, the compounds may be present in stereoisomeric forms, to which the present invention relates.

In view of their fungicidal activity, preferred compounds are those in which the substituents have the following meanings:

$R^1$ is hydrogen, $C_1$–$C_6$-alkyl, such as methyl, ethyl, propyl, 1-methylethyl, butyl, 1-methylpropyl, 2- methylpropyl, 1,1-dimethylethyl, pentyl or hexyl, in particular methyl or propyl, $C_1$–$C_3$-alkoxy-$C_1$- or $C_2$-alkyl, such as methoxymethyl, ethoxymethyl, propoxymethyl, methoxyethyl, ethoxyethyl or propoxyethyl, preferably methoxymethyl, phenyl, phenyl-$C_1$- or $C_2$-alkyl, such as benzyl, phenylethyl, in particular benzyl, phenoxy-$C_1$- or $C_2$-alkyl, such as phenoxymethyl or phenoxyethyl, in particular phenoxymethyl, where the three last-mentioned radicals may be monosubstituted, disubstituted or trisubstituted in the phenyl moiety by halogen, such as fluorine, chlorine, bromine or iodine, or by $C_1$–$C_4$-alkyl, such as methyl, ethyl, propyl, 1-methylethyl, butyl, 1-methylpropyl, 2-methylpropyl or 1,1-dimethylethyl, $R^2$ and $R^3$ independently of one another are each hydrogen, $C_1$–$C_3$-alkyl, such as methyl, ethyl, propyl or 1-methylethyl, in particular methyl or ethyl, phenyl which is monosubstituted, disubstituted or trisubstituted by halogen, such as fluorine, chlorine, bromine or iodine, or by $C_1$–$C_4$-alkyl, such as methyl, ethyl, propyl, 1-methylethyl, butyl, 1-methylpropyl, 2-methylpropyl or 1,1-dimethylethyl, $R^4$ is hydrogen, $R^5$ is hydrogen, $C_1$–$C_6$-alkyl, such as methyl, ethyl, propyl, 1-methylethyl, butyl, 1-methylpropyl, 2-methylpropyl, 1,1-dimethylethyl, pentyl or hexyl, in particular methyl, propyl or butyl, $C_3$–$C_6$-cycloalkyl, such as cyclopropyl, cyclobutyl, cyclopentyl or cyclohexyl, in particular cyclopentyl, $C_5$- or $C_6$-cycloalkyl-$C_1$–$C_3$-alkyl, such as cyclopentylmethyl, cyclohexylmethyl, cyclopentylethyl, cyclohexylethyl, cyclopentylpropyl or cyclohexylpropyl, in particular cyclopentylethyl, halogen, such as chlorine or bromine, in particular chlorine, phenyl, phenyl-$C_1$- or $C_2$-alkyl, such as benzyl or phenylethyl, in particular benzyl, where the two last-mentioned radicals may be monosubstituted, disubstituted or trisubstituted in the phenyl moiety by halogen, such as fluorine, chlorine, bromine or iodine, $C_1$–$C_4$-alkyl, such as methyl, ethyl, propyl or 1-methylethyl, butyl, 1-methylpropyl, 2-methylpropyl or 1,1-dimethylethyl, or $C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy, $C_1$–$C_3$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio, $R^6$ is hydrogen, $C_1$–$C_4$-alkyl, such as methyl, ethyl, propyl, 1-methylethyl, butyl, 1-methylpropyl, 2-methylpropyl or 1,1-dimethylethyl, in particular methyl or ethyl, halogen, such as fluorine, chlorine, bromine or iodine, in particular chlorine or bromine, phenyl, $C_1$–$C_3$-alkoxy, such as methoxy, ethoxy, propoxy, 1-methylethoxy, in particular methoxy, or $R^5$ and $R^6$ together form a polymethylene chain of the formula —$(CH_2)_m$— in which m is 3 or 4, $R^7$ is hydrogen, $C_1$–$C_6$-alkyl, such as methyl, ethyl, propyl, 1-methylethyl, butyl, 1-methylpropyl, 2-methylpropyl, 1,1-dimethylethyl, pentyl or hexyl, in particular methyl, ethyl, propyl, 1-methylethyl, butyl, 1-methylpropyl, 2-methylpropyl or 1,1-dimethylethyl, $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl or 5-hexenyl, in particular 2-propenyl, 2-butenyl, 3-butenyl, 1-methyl-2-propenyl, 2-methyl-2-propenyl or 3-methyl-2-butenyl, $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl or 5-hexynyl, in particular 2-propynyl or 2-butynyl, where the three last-mentioned radicals may be monosubstituted, disubstituted or trisubstituted by halogen, such as fluorine, chlorine, bromine or iodine, in particular fluorine or chlorine, $C_1$–$C_3$-alkoxy-$C_2$–$C_6$-alkyl, such as methoxyethyl, methoxypropyl, methoxybutyl, methoxypentyl, methoxyhexyl, ethoxyethyl, ethoxypropyl, ethoxybutyl, ethoxypentyl, ethoxyhexyl or propoxyethyl, in particular methoxyethyl, methoxypropyl or methoxybutyl, monocyclic or polycyclic $C_3$–$C_{10}$-cycloalkyl, such as cyclopropyl, cyclobutyl, cyclopentyl, cyclohexyl, cycloheptyl, cyclooctyl, menthyl, norbornyl, adamantyl or tricyclodecyl, in particular cyclopropyl or cyclohexyl, or monocyclic or polycyclic $C_3$–$C_{10}$-cycloalkylmethyl, such as cyclopropylmethyl, cyclobutylmethyl, cyclopentylmethyl, cyclohexylmethyl, cycloheptylmethyl or cyclooctylmethyl, in particular cyclopropylmethyl or cyclohexylmethyl, where these rings may carry one or two $C_1$–$C_4$-alkyl groups, such as methyl, ethyl, propyl, 1-methylethyl, butyl, 1-methylpropyl, 2-methylpropyl or 1,1-dimethylethyl, in particular methyl or ethyl, or phenyl, monocyclic or polycyclic $C_5$–$C_{10}$-cycloalkenyl, in particular 2-cyclohexen-1-yl, or monocyclic or polycyclic $C_5$–$C_{10}$-cycloalkenylmethyl, in particular 1-cyclohexenylmethyl, 2-cyclohexenylmethyl or 3-cyclohexenylmethyl, where these rings may carry one or two $C_1$–$C_4$-alkyl groups, such as methyl, ethyl, propyl, 1-methylethyl, butyl, 1-methylpropyl, 2-methylpropyl or 1,1-dimethylethyl, in particular methyl, or phenyl, phenyl, phenyl-$C_1$–$C_6$-alkyl, such as benzyl, 1-phenylethyl, 2-phenylethyl, 1-phenylpropyl, 2-phenylpropyl, 3-phenylpropyl, 1-methyl-1-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-1-phenylpropyl, 2-methyl-2-phenylpropyl, 2-methyl-3-phenylpropyl, 1,1-dimethyl-2-phenylethyl, 5-phenylpentyl or 6- phenylhexyl, in particular benzyl, 2-phenylethyl or 4-phenylbutyl, phenyl-$C_3$-$C_6$-alkenyl, in particular 3-phenyl-2-propenyl, 4-phenyl-2-butenyl or 4-phenyl-3-butenyl, phenoxy-$C_2$-$C_6$-alkyl, such as phenoxyethyl, phenoxypropyl, 2-phenoxy-2-methylethyl, phenoxybutyl, phenoxypentyl or phenoxyhexyl, in particular phenoxyethyl, 2-phenoxy-2-methylethyl or phenoxybutyl, where the four last-mentioned radicals may be monosubstituted, disubstituted or trisubstituted in the phenyl moiety by halogen, such as fluorine, chlorine, bromine or iodine, in particular fluorine or chlorine, $C_1$-$C_4$-alkyl, such as methyl, ethyl, propyl, 1-methylethyl, butyl, 1-methylpropyl, 2-methylpropyl or 1,1-dimethylethyl, in particular methyl, 1-methylethyl or 1,1-dimethylethyl, $C_1$-$C_3$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl, or $C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy, X is CH or N, Y is

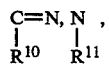

$R^{10}$ is hydrogen or $C_1$-$C_4$-alkyl, such as methyl, ethyl, propyl, 1-methylethyl, butyl, 1-methylpropyl, 2-methylpropyl or 1,1-dimethylethyl, in particular methyl, $R^{11}$ is hydrogen, $C_1$-$C_4$-alkyl, such as methyl, ethyl, propyl, 1-methylethyl, butyl, 1-methylpropyl, 2-methylpropyl or 1,1-dimethylethyl, in particular methyl, $C_3$-$C_8$-cycloalkyl, such as cyclopropyl, cyclobutyl, cyclopentyl, cyclohexyl, cycloheptyl or cyclooctyl, in particular cyclopentyl or cyclohexyl, where the cycloalkyl radical may be monosubstituted or disubstituted by $C_1$-$C_4$-alkyl, such as methyl, ethyl, propyl, 1-methylethyl, butyl, 1-methylpropyl, 2-methylpropyl or 1,1-dimethylethyl, in particular methyl or ethyl, or monosubstituted by phenyl, phenyl, phenyl-$C_1$- or $C_2$-alkyl, such as benzyl or phenylethyl, in particular benzyl, where the two last-mentioned radicals may be monosubstituted, disubstituted or trisubstituted in the phenyl moiety by halogen, such as fluorine, chlorine, bromine or iodine, in particular fluorine or chlorine, $C_1$-$C_4$-alkyl, such as methyl, ethyl, propyl, 1-methylethyl, butyl, 1-methylpropyl, 2-methylpropyl or 1,1-dimethylethyl, in particular methyl, 1-methylethyl or 1,1-dimethylethyl, $C_1$-$C_3$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl, or $C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy.

Suitable acid addition salts are the plant-tolerated salts of acids which do not adversely affect the fungicidal activity of I, for example the iodides, chlorides, bromides, sulfates, dodecylsulfates, nitrates, carbonates, phosphates, borates, formates, acetates, propionates, benzoates, oxalates, naphthalenesulfonates, dodecylbenzenesulfonates, lactates, citrates and the salts with the anion of saccharine.

Suitable metal complexes are the complexes of copper, of zinc, of tin, of manganese, of iron, of cobalt or of nickel. The complexes are preferably prepared from the free bases I and the salts of the metals with mineral acids, for example the chlorides or sulfates.

The present invention furthermore relates to a process for the preparation of the substituted pyridine derivatives of the formula I, wherein 1. a compound of the formula II

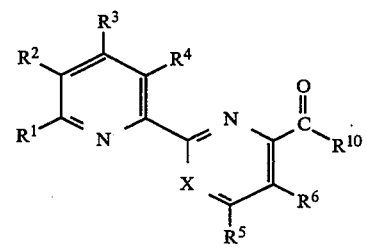

where $R^1$-$R^4$, $R^{10}$ and X have the meanings as in formula I as claimed in claim 1 or 2, is reacted with a hydroxylamine salt, such as hydroxylammonium chloride or sulfate, in the presence of a base, such as a carbonate or bicarbonate of an alkali metal or alkaline earth metal, for example in a protic solvent, such as an alcohol or an alcohol/water mixture, for example at from 10° to 100° C., preferably from 10° to 70° C., to give an oxime of the formula I a

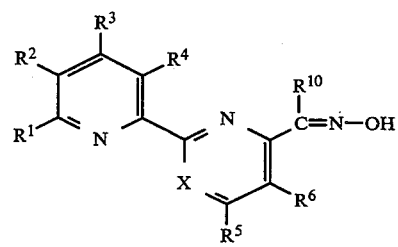

and the latter is converted by means of a base, such as sodium hydride or potassium hydroxide, into an oxime salt of the formula I b

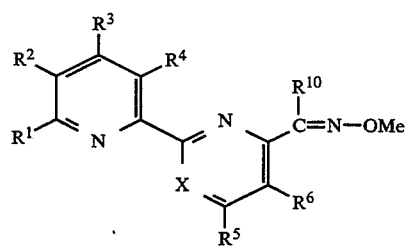

where Me is an alkali metal or alkaline earth metal atom, such as sodium or potassium, and the oxime salt of the formula I b is reacted with a compound of the formula III $$R^7-X' \quad \text{III}$$

where $R^7$ has the meanings as in formula I as claimed in claim 1 or 2 and X' is a nucleofugic leaving group, such as halogen, tosylate or mesylate, preferably chlorine, bromine or iodine, for example in an inert solvent, such as acetonitrile, dichloromethane, 1,2-dichloroethane, toluene, xylene, tetrahydrofuran, dioxane, diethylene glycol dimethyl ether, dimethylformamide or N-methylpyrrolidone, for example at from −30° to 160° C., preferably from −10° to 110° C., to give a compound of the formula I c

[Structure Ic: pyridine with substituents $R^1, R^2, R^3, R^4$ connected via $-CH=N-C(R^{10})=N-O-R^7$ group, with $X, R^5, R^6$ substituents]

or 2. a compound of the formula IV a $$H_2N-O-R^7 \cdot HA \quad \text{IV a}$$

is reacted with a compound of the formula II

[Structure II: pyridine with $R^1, R^2, R^3, R^4$ connected via $-CH=N-C(=O)-R^{10}$ with $X, R^5, R^6$]

or with a compound of the formula V

[Structure V: pyridine with $R^1, R^2, R^3, R^4$ connected via $-CH=N-C(OR^{12})(OR^{12})-R^{10}$ with $X, R^5, R^6$]

where $R^1$–$R^7$, $R^{10}$ and X have the meanings as in formula I as claimed in claim 1 or 2, HA is an inorganic or organic acid, such as hydrochloric acid, sulfuric acid or acetic acid, and $R^{12}$ is $C_1$–$C_4$-alkyl, such as methyl, ethyl, propyl or butyl, in particular methyl or ethyl, or the two radicals $R^{12}$ together form a polymethylene chain of the formula —$(CH_2)_n$— in which n is 2 or 3, for example in a protic solvent, such as an alcohol or alcohol/water mixture, in the presence or absence of a base, such as a carbonate or bicarbonate of an alkali metal or alkaline earth metal, for example at from 10° to 110° C., preferably from 20° to 80° C., to give a compound of the formula Ic, or 3. a compound of the formula VI

[Structure VI: pyridine with $R^1, R^2, R^3, R^4$ connected via $-CH=N-C(Z)=$ with $X, R^5, R^6$]

is reacted with a compound of the formula IV b or c $$\underset{R^{11}}{HN}-O-R^7 \quad \text{IV b}$$

$$\underset{R^{11}}{HN}-O-R^7 \cdot HA \quad \text{IV c}$$

where $R^1$–$R^7$, $R^{11}$ and X have the meanings as in the formula I as claimed in claim 1 or 2, Z is halogen, such as fluorine, chlorine, bromine or iodine, preferably chlorine or bromine, and HA is an inorganic or organic acid, such as hydrochloric acid, sulfuric acid or acetic acid, in a solvent, such as ethanol, isopropanol, acetonitrile, dichloromethane, 1,2-dichloroethane, toluene, xylene, tetrahydrofuran, dioxane, diethylene glycol dimethyl ether, dimethylformamide or N-methylpyrrolidone, for example at from −10° C. to the boiling point of the solvent, in the presence or absence of a base, such as a carbonate or bicarbonate of an alkali metal or alkaline earth metal, sodium hydride, an alkali metal hydroxide or alcoholate, a tertiary amine, pyridine or 4-dimethylaminopyridine. In the case of compounds of the formula VI where X is CH, it may be particularly advantageous first to replace the halogen group with a particularly readily displaceable leaving group, e.g. methylsulfinyl or methylsulfonyl, and then to carry out the reaction with a compound of the formula IV b or IV c.

The compounds of the formula III are generally known compounds of organic chemistry.

The compounds of the formula IV a–c are known or can be prepared in a known manner (for example Houben-Weyl, Methoden der Organischen Chemie, 4th Edition, Vol. E 16a, page 214 et seq. [IV a] and page 271 et seq. [IV b, c]).

The compounds of the formula VI are known or can be prepared in a known manner (e.g. European Patents 234,104, 259,139, 270,362 and 407,899 and J. Org. Chem. 32 (1967), 1591).

The compounds of the formulae II and V

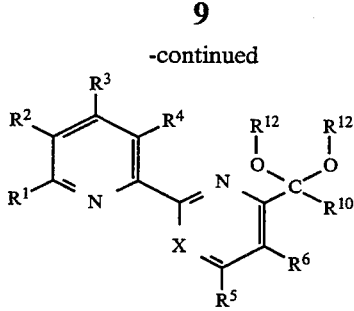

which are used as intermediates in the preparation of the compounds of the formula I c and in which $R^1$ is hydrogen, $C_1$-$C_6$-alkyl, $C_1$-$C_4$-alkoxy-$C_1$-$C_4$-alkyl, $C_1$-$C_4$-alkylthio-$C_1$-$C_4$-alkyl, $C_2$-$C_6$-alkenyl, $C_2$-$C_6$-alkynyl, $C_3$-$C_7$-cycloalkyl, where the cycloalkyl radical may be monosubstituted, disubstituted or trisubstituted by $C_1$-$C_4$-alkyl, or halogen, phenyl, phenoxy-$C_1$-$C_4$-alkyl, phenylmercapto-$C_1$-$C_4$-alkyl, phenyl-$C_1$-$C_4$-alkyl, phenoxy or phenylmercapto, where the six last-mentioned radicals may be monosubstituted, disubstituted or trisubstituted in the phenyl moiety by halogen, nitro, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy, $R^2$, $R^3$ and $R^4$ independently of one another are each hydrogen, $C_1$-$C_6$-alkyl or phenyl where the phenyl radical may be monosubstituted, disubstituted or trisubstituted by halogen, nitro, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy, $R^5$ is hydrogen, $C_1$-$C_6$-alkyl, $C_3$-$C_7$-cycloalkyl, $C_3$-$C_7$-cycloalkyl-$C_1$-$C_4$-alkyl, where the two last-mentioned radicals may be monosubstituted, disubstituted or trisubstituted in the cycloalkyl moiety by $C_1$-$C_4$-alkyl, or $C_1$-$C_4$-haloalkyl, $C_1$-$C_4$-alkoxy, $C_1$-$C_4$-alkylthio, $C_1$-$C_4$-alkoxy-$C_1$-$C_4$-alkyl, $R^8R^9N$—, $C_1$-$C_4$-alkylthio-$C_1$-$C_4$-alkyl, hydroxyl, halogen, $C_2$-$C_6$-alkenyl, $C_2$-$C_6$-alkynyl, $C_3$-$C_6$-alkenyloxy, $C_3$-$C_6$-alkynyloxy, phenyl, phenoxy, phenyl-$C_1$-$C_4$-alkyl, phenoxy-$C_1$-$C_4$-alkyl, phenylmercapto-$C_1$-$C_4$-alkyl or phenylmercapto, where the six last-mentioned radicals may be monosubstituted, disubstituted or trisubstituted in the phenyl moiety by halogen, nitro, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy, $R^6$ is hydrogen, $C_1$-$C_4$-alkyl, $C_1$-$C_4$-alkoxy, $C_1$-$C_4$-alkoxycarbonyl, halogen or phenyl, where the phenyl radical may be monosubstituted, disubstituted or trisubstituted by halogen, nitro, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy, or $R^5$ and $R^6$ together form a polymethylene chain of the formula —$(CH_2)_m$— in which m is 3 or 4, $R^8$ and $R^9$ independently of one another are each hydrogen, $C_1$-$C_6$-alkyl, $C_3$-$C_6$-alkenyl, $C_3$-$C_6$-alkynyl, $C_3$-$C_7$-cycloalkyl, where the cycloalkyl radical may be monosubstituted, disubstituted or trisubstituted by $C_1$-$C_4$-alkyl, or phenyl or phenyl-$C_1$-$C_4$-alkyl, where the two last-mentioned radicals may be monosubstituted, disubstituted or trisubstituted in the phenyl moiety by halogen, nitro, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy, or the two radicals $R^8$ and $R^9$ together with the nitrogen atom to which they are bonded, form an unsubstituted or monosubstituted, disubstituted, trisubstituted or tetrasubstituted 5- to 7-membered, saturated or unsaturated heterocyclic structure having 1 to 3 identical or different hetero atoms, preferably nitrogen, oxygen and/or sulfur, and the substituent $C_1$-$C_4$-alkyl, X is CH or N, $R^{10}$ is hydrogen or $C_1$-$C_6$-alkyl and $R^{12}$ is $C_1$-$C_4$-alkyl or the two radicals $R^{12}$ together form a polymethylene chain of the formula —$(CH_2)_n$— in which n is 2 or 3, are novel, with the exception of the compounds 6-formyl-2,2'-bipyridine, 6-acetyl-2,2'-bipyridine, 6-formyl-4-methoxy-2,2'-bipyridine and 6-formyl-4-hydroxy-2-(2-pyridyl)-pyrimidine, and form part of the present invention.

Of the compounds II and V, preferered intermediates for the preparation of compounds of the formula I c are those in which the substituents have the following meanings:

$R^1$ is hydrogen, $C_1$-$C_6$-alkyl, $C_1$-$C_3$-alkoxy-$C_1$- or $C_2$-alkyl, phenyl, phenyl-$C_1$- or $C_2$-alkyl or phenoxy-$C_1$- or $C_2$-alkyl, where the three last-mentioned radicals may be monosubstituted, disubstituted or trisubstituted in the phenyl moiety by halogen or $C_1$-$C_4$-alkyl, $R^2$ and $R^3$ independently of one another are each hydrogen, $C_1$-$C_3$-alkyl or phenyl, where the phenyl radical may be monosubstituted, disubstituted or trisubstituted by halogen or $C_1$-$C_4$-alkyl, $R^4$ is hydrogen, $R^5$ is hydrogen, $C_1$-$C_6$-alkyl, $C_3$-$C_6$-cycloalkyl, $C_5$- or $C_6$-cycloalkyl-$C_1$-$C_3$-alkyl, halogen, phenyl or phenyl-$C_1$- or $C_2$-alkyl, where the two last-mentioned radicals may be unsubstituted or monosubstituted, disubstituted or trisubstituted in the phenyl moiety by halogen, $C_1$-$C_4$-alkyl or $C_1$-$C_4$-alkoxy, or $R^5$ is $C_1$-$C_3$-haloalkyl, $C_1$-$C_4$-alkoxy or $C_1$-$C_4$-alkylthio, $R^6$ is hydrogen, $C_1$-$C_4$-alkyl, halogen, phenyl or $C_1$-$C_3$-alkoxy or $R^5$ and $R^6$ together form a polymethylene chain of the formula —$(CH_2)_m$— in which m is 3 or 4, X is CH or N, $R^{10}$ is hydrogen or $C_1$-$C_4$-alkyl and $R^{12}$ is $C_1$-$C_4$-alkyl or the two radicals $R^{12}$ together form a polymethylene chain of the formula —$(CH_2)_n$— in which n is 2 or 3.

The present invention furthermore relates to a process for the preparation of the compounds II, wherein
1. a compound of the formula V

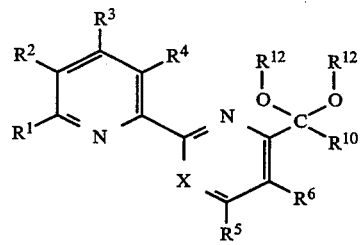

is hydrolyzed in a known manner (for example Houben-Weyl, Methoden der Organischen Chemie, 4th Edition, Vol. E 3, page 362 et seq.) in the presence of an inorganic or organic acid, such as hydrochloric acid, sulfuric acid, formic acid or acetic acid, in the presence or absence of a solvent, such as water, acetone, methanol, ethanol, isopropanol, dioxane, tetrahydrofuran, acetonitrile or dimethylformamide, for example at from 20° to 100° C., or
2. a compound of the formula VII

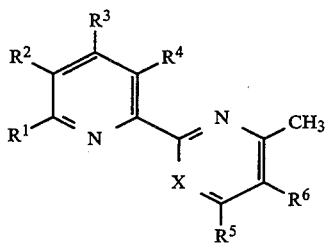

where $R^1$-$R^6$ and X have the meanings as in formula I as claimed in claim 1 or 2, is reacted in a conventional manner (for example Houben-Weyl, Methoden der Organischen Chemie, 4th Edition, Vol. E 3, page 231 et seq.) with an oxidizing agent, e.g. $SeO_2$ in ethanol, tert-butanol, dioxane, pyridine or acetic acid, for example at from 20° C. to the boiling point of the solvent, to give a compound of the formula IIa

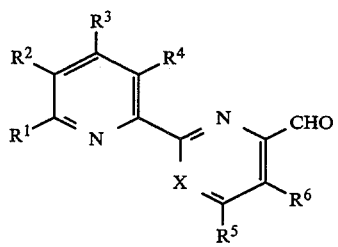

or
3. a compound of the formula VI a

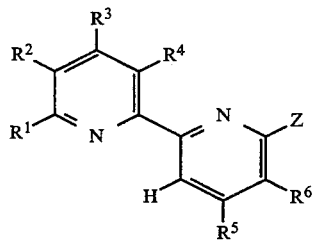

where $R^1$-$R^6$ have the meanings as in the formula I as claimed in claim 1 or 2, and Z is halogen, such as fluorine, chlorine, bromine or iodine, preferably bromine or iodine, is reacted in a conventional manner (for example Houben-Weyl, Methoden der Organischen Chemie, 4th Edition, Vol. E 3, page 115 et seq. and page 130 et seq.) a) with an organolithium compound of the formula VIII $$R^{13}-Li \qquad \text{VIII}$$

where $R^{13}$ is $C_1$-$C_6$-alkyl, such as methyl, ethyl, propyl, 1-methylethyl, butyl, 1-methylpropyl, 2-methylpropyl, 1,1-dimethylethyl, pentyl or hexyl, in particular butyl, 1-methylpropyl or 1,1-dimethylethyl, or phenyl, in a solvent, such as diethyl ether, tetrahydrofuran, pentane or hexane, or a mixture of the stated solvents, at from −90° to 0° C., particularly from −80° to to −40° C., to give a compound of the formula IX a

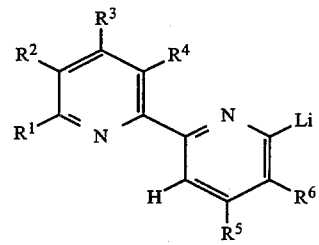

or
b) with Mg in a solvent, such as diethyl ether or tetrahydrofuran, at from 0° to 40° C. to give a compound of the formula IX b

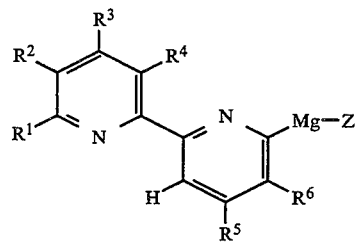

and the organometallic compound of the formula IX a or IX b is reacted with a compound of the formula X

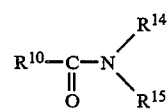

where $R^{10}$ has the meanings as in the formula I as claimed in claim 1 or 2 and $R^{14}$ and $R^{15}$ independently of one another are each $C_1$-$C_4$-alkyl, such as methyl, ethyl, propyl, 1-methylethyl, butyl, 1-methylpropyl, 2-methylpropyl or 1,1-dimethylethyl, in particular methyl, $C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy, or $C_5$-$C_7$-cycloalkyl, such as cyclopentyl, cyclohexyl or cycloheptyl, or $R^{14}$ and $R^{15}$, together with the nitrogen atom to which they are bonded, form a 5-membered to 7-membered heterocyclic structure having 1 or 2 identical or different hetero atoms, preferably nitrogen and/or oxygen, in particular piperidine or morpholine.

Compounds of the formula VII are known or can be prepared in a known manner (for example European Patent 234,104, U.S Pat. No. 4,927,827 or Tetrahedron Lett. 31 (1990), 4625).

Compounds of the formula VIa are known or can be prepared in a known manner (for example J. Organomet. Chem. 56 (1973), 53 or Tetrahedron Lett. 31 (1990), 4625).

Compounds of the formula VIII are known and are readily obtainable (for example Houben-Weyl, Methoden der Organischen Chemie, 4th Edition, Vol. 13, 1, page 87 et seq.).

Compounds of the formula X are generally known compounds of organic chemistry.

The present invention furthermore relates to a process for the preparation of a compound V a

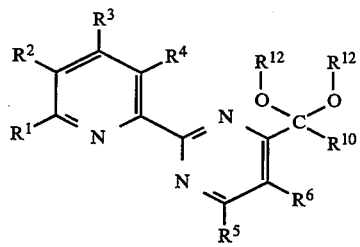

Va where $R^1$–$R^6$, $R^{10}$ and $R^{12}$ have the meanings as in formula V as claimed in claim 9 or 10, wherein a picolinamidine derivative of the formula XI a or XI b

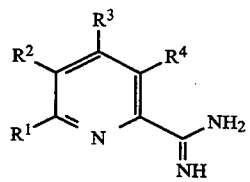

XIa

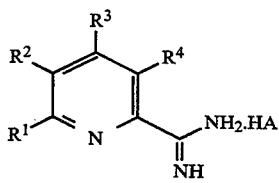

XIb where $R^1$–$R^4$ have the meanings as in formula I as claimed in claim 1 or 2 and HA is an inorganic or organic acid, such as hydrochloric acid, sulfuric acid or acetic acid, is reacted in a polar solvent, such as water, methanol, ethanol, tert-butanol, acetonitrile or dimethylformamide, and in the presence or absence of a base, such as sodium methylate or ethylate, triethylamine or a carbonate or bicarbonate of an alkali metal or alkaline earth metal, for example at from −10° C. to the boiling point of the solvent,
1) with a dicarbonyl compound of the formula XII

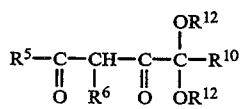

XII or
2) with a ketone of the formula XIII

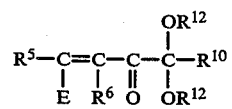

XIII where $R^6$ and $R^{10}$ have the meanings as in formula I as claimed in claim 1, $R^5$ has the meanings as in formula I as claimed in claim 1, with the exception of $NR^8R^9$, hydroxyl and halogen, $R^{12}$ has the meanings as in the formula V as claimed in claim 9 or 10, E is $OR^{16}$ or $NR^{17}R^{18}$, $R^{16}$ is $C_1$–$C_4$-alkyl, such as methyl, ethyl, propyl, 1-methylethyl, butyl, 1-methylpropyl, 2-methylpropyl or 1,1-dimethylethyl, in particular methyl, and $R^{17}$ and $R^{18}$ independently of one another are each hydrogen, or $C_1$–$C_4$-alkyl, such as methyl, ethyl, propyl, 1-methylethyl, butyl, 1-methylpropyl, 2-methylpropyl or 1,1-dimethylethyl, in particular methyl, or $R^{17}$ and $R^{18}$, together with the nitrogen atom to which they are bonded, form a 5-membered to 7-membered heterocyclic structure having 1 or 2 identical or different hetero atoms, preferably nitrogen and/or oxygen, in particular pyrrolidine, piperidine or morpholine, and, if required, the resulting compound of the formula V a in which $R^5$ is hydroxyl is reacted in a conventional manner (for example as described in European Patents 259,139 and 270,362) with a halogenating agent, such as thionyl chloride, phosgene, phosphoryl chloride, phosphorus pentachloride, phosphoryl bromide or phosphorus tribromide, in the presence or absence of a diluent, such as benzene, toluene or chlorobenzene, for example at from 50° to 150° C., to give a compound of the formula V a in which $R^5$ is halogen, such as fluorine, chlorine, bromine or iodine, in particular chlorine or bromine.

The compounds of the formula V a which are obtained in this manner and in which $R^5$ is halogen, such as fluorine, chlorine, bromine or iodine, in particular chlorine or bromine, may, if required, be reacted with a compound of the formula XIV $$R^5\text{—M} \qquad\qquad XIV$$

where $R^5$ is $C_1$–$C_4$-alkoxy, $C_1$–$C_4$-alkylthio, $NR^8R^9$, $C_3$–$C_6$-alkenyloxy, $C_3$–$C_6$-alkynyloxy, phenoxy or phenylmercapto, preferably $C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy, or $C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio, M is hydrogen or an alkali metal atom, such as sodium or potassium, in particular sodium, and $R^8$ and $R^9$ have the meanings as in the formula I as claimed in claim 1, in the presence or absence of a base, such as a carbonate or a bicarbonate of an alkali metal or an alkaline earth metal or a tertiary amine, in a solvent, e.g. methanol, ethanol, tetrahydrofuran, dioxane, acetonitrile, water or a mixture of water and one of the stated solvents, at from 10° C. to the boiling point of the solvent, to give a compound of the formula V a.

The picolinamidine derivatives of the formula XI a or XI b are known or can be prepared by methods similar to known ones (for example as described in European Patents 259,139 and 270,362).

The dicarbonyl compounds of the formula XII and the ketones of the formula XIII are known or can be prepared in a known manner (for example as described in Chem. Ber. 97 (1964), 3407 or British Patent 2,095,240).

The compounds of the formula I and the salts and metal complexes thereof are suitable as fungicides.

Preparation Examples

EXAMPLE 1

4-Formyloximino-2-(2-pyridyl)-pyrimidine (compound Ic)

0.75 g (10.8 mmol) of hydroxylammonium chloride and 1.82 g (21.6 mmol) of sodium bicarbonate are added to a solution of 2 g (10.8 mmol) of 4-formyl-2-(2-pyridyl)pyrimidine in 50 ml of methanol. After stirring has been carried out for 12 hours at room temperature (20° C.), 100 ml of saturated $NH_4Cl$ solution are added to the reaction mixture, extraction is effected with three times 50 ml of dichloromethane and the combined organic phases are dried over sodium sulfate. After the solvent has been distilled off under reduced pressure, an orange solid is obtained.
Yield: 46% of theory, mp.=190° C.

If 6-formyl-4-methyl-2-(6-methyl-2-pyridyl)pyrimidine is used instead of 4-formyl-2-(2-pyridyl)pyrimidine and O-n-butylhydroxylammonium chloride instead of hydroxylammonium chloride, 6-formyl-O-n-butyloximino-4-methyl-2-(6-methyl-2-pyridyl)-pyrimidine (compound 133c) is obtained in a corresponding manner.

A yellowish oil is obtained in a yield of 50% of theory after chromatography over alumina (n-hexane/methyl tert-butyl ether).
IR: 2959, 1577, 1535, 1365, 1046 cm$^{-1}$.

If 6-formyl-2,2'-bipyridine is used instead of 4-formyl-2-(2-pyridyl)-pyrimidine and O-phenylbutylhydroxylammonium chloride instead of hydroxylammonium chloride, 6-formyl-O-4-phenylbutyloximino-2,2'-bipyridine (compound 105c) is obtained in a corresponding manner.
Yield: 76% of theory, mp.=76°-78° C.

The compounds listed in Table 1 can be prepared in a corresponding manner.

EXAMPLE 2

5-Chloro-4-O-isobutylhydroxylamino-6-methyl-2-(6-methyl-2-pyridyl)-pyrimidine (compound 66d)

A mixture of 1.11 g (11 mmol) of triethylamine and 25 ml of ethanol is added dropwise to a suspension of 1.38 g (11 mmol) of O-isobutylhydroxylammonium chloride in 25 ml of ethanol. After stirring has been carried out for 15 minutes at room temperature, 2.54 g (10 mmol) of 4,5-dichloro-6-methyl-2-(6-methyl-2-pyridyl)-pyrimidine are added and the reaction mixture is then refluxed for 6 hours. The solvent is distilled off under reduced pressure and the residue is purified by chromatography over alumina (n-hexane/methyl tert-butyl ether). The title compound is obtained in the form of orange crystals.
Yield: 65% of theory, mp.=108°-110° C.

The compounds listed in Table 2 can be prepared in a corresponding manner.
Preparation of the intermediates

EXAMPLE 3

4-Formyldimethylacetal-2-(2-pyridyl)-pyrimidine (compound 1.3)

A solution of 40 g (0.25 mol) of 2-pyridylamidine hydrochloride in 100 ml of methanol is added to a solution of sodium methylate in methanol, prepared from 7 g (0.3 mol) of sodium and 200 ml of methanol, and stirring is carried out for 10 minutes at room temperature. Thereafter, a solution of 43.9 g (0.25 mol) of (β-dimethylaminovinyl)glyoxal dimethylacetal in 100 ml of methanol is added dropwise and the mixture is refluxed. for 7 hours. The reaction mixture is then evaporated down under reduced pressure and neutralized with water/acetic acid. Extraction with three times 150 ml of dichloromethane, subsequent washing with water (3×50 ml), drying over sodium sulfate and removal of the solvent by distillation under reduced pressure give the title compound in the form of brownish crystals.
Yield: 47% of theory, mp.=42° C.

If 6-methyl-2-pyridylamidine hydrochloride is used instead of 2-pyridylamidine hydrochoride and diethoxyacetylacetone instead of (β-dimethylaminovinyl)-glyoxal dimethyl acetal, 4-formyldiethylacetal-6-methyl-2-(6-methyl-2-pyridyl)-pyrimidine (compound 4.3) is obtained in a corresponding manner.

A yellow oil which slowly crystallizes on standing is obtained in a yield of 27% of theory.
IR: 2975, 1581, 1372, 1112, 1062 cm$^{-1}$.

The compounds listed in Table 3 can be prepared in a corresponding manner.

EXAMPLE 4

4-Formyl-2-(2-pyridyl)-pyrimidine (compound 1.4)

A solution of 10 g (43.3 mmol) of 4-formyldimethylacetal-2-(2-pyridyl)-pyrimidine in 43.3 ml of 1N hydrochloric acid is heated at the boil for 2 hours. After cooling, neutralization is effected by means of Na$_2$CO$_3$ solution and extraction is carried out with three times 50 ml of dichloromethane. The combined organic phases are dried over sodium sulfate and the solvent is distilled off under reduced pressure, after which the title compound remains in the form of brownish crystals.
Yield: 62% of theory, mp.=110°-112° C.

If 4-formyldiethylacetal-6-methyl-2-(6-methyl-2-pyridyl)-pyrimidine is used instead of 4-formyldimethylacetal-2-(2-pyridyl)-pyrimidine, 4-formyl-6-methyl-2-(6-methyl-2-pyridyl)-pyrimidine (compound 3.4) is obtained in a corresponding manner.

A brownish resin is obtained in a yield of 69% of theory.

The compounds listed in Table 4 can be prepared in a corresponding manner.

EXAMPLE 5

6-Formyl-2,2'-bipyridine (compound known from Aust. J. Chem. 44 (1991), 331)

A solution of 7.05 g (30 mmol) of 6-bromo-2,2'-bipyridine in 50 ml of diethyl ether is added to a solution of 19.4 ml (31 mmol) of 1.6M butyllithium-in-hexane solution in 100 ml of diethyl ether at −80° C. under a nitrogen atmosphere. After the addition is complete, stirring is carried out for a further 30 minutes at this temperature, after which a solution of 4.39 g (60 mmol) of dimethylformamide in 30 ml of diethyl ether is added at from −80° to −90° C. After further stirring at this temperature for 1.5 hours, hydrolysis is carried out with 150 ml of quarter-concentrated hydrochloric acid at from −60° to −50° C. The reaction mixture is then neutralized at room temperature by adding solid sodium bicarbonate, the phases are separated and the aqueous phase is extracted once again with 50 ml of diethyl ether. The organic phases are combined and are dried over sodium sulfate and finally the solvent is distilled off under reduced pressure. The title compound is obtained as a reddish brown oil which crystallizes on standing.
Yield: 96% of theory, mp.=41°-43° C.

The compounds listed in Table 4 can be prepared in a corresponding manner.

TABLE 1

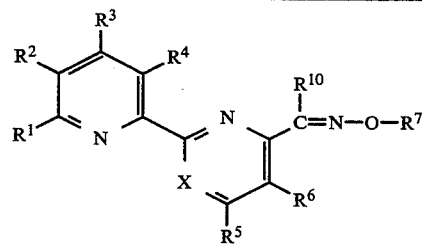

Ic

| Comp No. | R¹ | R² | R³ | R⁴ | R⁵ | R⁶ | R⁷ | R¹⁰ | X | mp./Ir (film) [cm⁻¹] |
|---|---|---|---|---|---|---|---|---|---|---|
| 1c | H | H | H | H | H | H | H | H | N | 190° C. |
| 2c | H | H | H | H | H | H | H | $CH_3$ | N | |
| 3c | H | H | H | H | H | H | $CH_3$ | H | N | 93° C. |
| 4c | H | H | H | H | H | H | $CH_3$ | $CH_3$ | N | |
| 5c | H | H | H | H | H | H | $C_2H_5$ | H | N | |
| 6c | H | H | H | H | H | H | $C_2H_5$ | $CH_3$ | N | |
| 7c | H | H | H | H | H | H | $n\text{-}C_3H_7$ | H | N | |
| 8c | H | H | H | H | H | H | $n\text{-}C_3H_7$ | $CH_3$ | N | |
| 9c | H | H | H | H | H | H | $n\text{-}C_4H_9$ | H | N | |
| 10c | H | H | H | H | H | H | $n\text{-}C_4H_9$ | $CH_3$ | N | |
| 11c | H | H | H | H | H | H | $i\text{-}C_4H_9$ | H | N | |
| 12c | H | H | H | H | H | H | $i\text{-}C_4H_9$ | $CH_3$ | N | |
| 13c | H | H | H | H | H | H | $t\text{-}C_4H_9$ | H | N | |
| 14c | H | H | H | H | H | H | $t\text{-}C_4H_9$ | $CH_3$ | N | |
| 15c | H | H | H | H | H | H | $CH_2-CH=CH_2$ | H | N | |
| 16c | H | H | H | H | H | H | $CH_2-CH=CH_2$ | $CH_3$ | N | |
| 17c | H | H | H | H | H | H | $CH_2CH=CH-CH_3$ | H | N | |
| 18c | H | H | H | H | H | H | $CH_2CH=CH-CH_3$ | $CH_3$ | N | |
| 19c | H | H | H | H | H | H | $CH_2-C(CH_3)=CH_2$ | H | N | |
| 20c | H | H | H | H | H | H | $CH_2-C(CH_3)=CH_2$ | $CH_3$ | N | |
| 21c | H | H | H | H | H | H | $CH_2-CH=CH-Cl$ | H | N | |
| 22c | H | H | H | H | H | H | $CH_2-CH=CH-Cl$ | $CH_3$ | N | |
| 23c | H | H | H | H | H | H | $CH_2-C(Cl)=CH_2$ | H | N | |
| 24c | H | H | H | H | H | H | $CH_2-C(Cl)=CH_2$ | $CH_3$ | N | |
| 25c | H | H | H | H | H | H | $CH_2-C\equiv CH$ | H | N | |
| 26c | H | H | H | H | H | H | $CH_2-C\equiv CH$ | $CH_3$ | N | |
| 27c | H | H | H | H | H | H | $(CH_2)_2-OCH_3$ | H | N | |
| 28c | H | H | H | H | H | H | $(CH_2)_2-OCH_3$ | $CH_3$ | N | |
| 29c | H | H | H | H | H | H | $(CH_2)_4-OCH_3$ | H | N | |
| 30c | H | H | H | H | H | H | $(CH_2)_4-OCH_3$ | $CH_3$ | N | |
| 31c | H | H | H | H | H | H | $cyclo\text{-}C_6H_{11}$ | H | N | |
| 32c | H | H | H | H | H | H | $cyclo\text{-}C_6H_{11}$ | $CH_3$ | N | |
| 33c | H | H | H | H | H | H | $C_6H_5$ | H | N | |
| 34c | H | H | H | H | H | H | $C_6H_5$ | $CH_3$ | N | |
| 35c | H | H | H | H | H | H | $C_6H_5CH_2$ | H | N | |
| 36c | H | H | H | H | H | H | $C_6H_5CH_2$ | $CH_3$ | N | |
| 37c | H | H | H | H | H | H | $4\text{-}Cl-C_6H_4CH_2$ | H | N | |
| 38c | H | H | H | H | H | H | $4\text{-}Cl-C_6H_4CH_2$ | $CH_3$ | N | |
| 39c | H | H | H | H | H | H | $4\text{-}F-C_6H_4CH_2$ | H | N | |
| 40c | H | H | H | H | H | H | $4\text{-}F-C_6H_4CH_2$ | $CH_3$ | N | |
| 41c | H | H | H | H | H | H | $C_6H_5CH_2CH_2$ | H | N | |
| 42c | H | H | H | H | H | H | $C_6H_5CH_2CH_2$ | $CH_3$ | N | |
| 43c | H | H | H | H | H | H | $C_6H_5(CH_2)_4$ | H | N | |
| 44c | H | H | H | H | H | H | $C_6H_5(CH_2)_4$ | $CH_3$ | N | |
| 45c | H | H | H | H | H | H | $4\text{-}Cl-C_6H_4(CH_2)_4$ | H | N | 52-53° C. |
| 46c | H | H | H | H | H | H | $4\text{-}Cl-C_6H_4(CH_2)_4$ | $CH_3$ | N | |
| 47c | H | H | H | H | H | H | $C_6H_5CH=CH-CH_2$ | H | N | |
| 48c | H | H | H | H | H | H | $C_6H_5CH=CH-CH_2$ | $CH_3$ | N | |
| 49c | H | H | H | H | H | H | $4\text{-}Cl-C_6H_4CH=CH-CH_2$ | H | N | |
| 50c | H | H | H | H | H | H | $4\text{-}Cl-C_6H_4CH=CH-CH_2$ | $CH_3$ | N | |
| 51c | H | H | H | H | H | H | $4\text{-}Cl-C_6H_4CH=CH-(CH_2)_2$ | H | N | 75-77° C. |
| 52c | H | H | H | H | H | H | $4\text{-}Cl-C_6H_4CH=CH-(CH_2)_2$ | $CH_3$ | N | |
| 53c | H | H | H | H | H | H | $4\text{-}Cl-C_6H_4CH_2-CH=CH-CH_2$ | H | N | 100° C. |
| 54c | H | H | H | H | H | H | $4\text{-}Cl-C_6H_4CH_2-CH=CH-CH_2$ | $CH_3$ | N | |
| 55c | H | H | H | H | H | H | $2\text{-}F-C_6H_4OCH_2CH_2$ | H | N | |
| 56c | H | H | H | H | H | H | $2\text{-}F-C_6H_4OCH_2CH_2$ | $CH_3$ | N | |
| 57c | H | H | H | H | H | H | $4\text{-}Cl-C_6H_4OCH(CH_3)CH_2$ | H | N | |
| 58c | H | H | H | H | H | H | $4\text{-}Cl-C_6H_4OCH(CH_3)CH_2$ | $CH_3$ | N | |
| 59c | H | H | H | H | H | H | $C_6H_5O(CH_2)_4$ | H | N | |
| 60c | H | H | H | H | H | H | $C_6H_5O(CH_2)_4$ | $CH_3$ | N | |
| 61c | H | H | H | H | H | H | $cyclo\text{-}C_6H_{11}CH_2$ | H | N | |
| 62c | H | H | H | H | H | H | $cyclo\text{-}C_6H_{11}CH_2$ | $CH_3$ | N | |
| 63c | H | H | H | H | H | H | H | H | CH | >200° C. |
| 64c | H | H | H | H | H | H | H | $CH_3$ | CH | |
| 65c | H | H | H | H | H | H | $CH_3$ | H | CH | 49 to 50° C. |
| 66c | H | H | H | H | H | H | $CH_3$ | $CH_3$ | CH | |
| 67c | H | H | H | H | H | H | $C_2H_5$ | H | CH | |
| 68c | H | H | H | H | H | H | $C_2H_5$ | $CH_3$ | CH | |

TABLE 1-continued

Ic structure: pyridine with R¹, R², R³, R⁴ substituents linked to a second ring bearing R⁵, R⁶, X, and a C(R¹⁰)=N—O—R⁷ group

| Comp No. | R¹ | R² | R³ | R⁴ | R⁵ | R⁶ | R⁷ | R¹⁰ | X | mp./Ir (film) [cm⁻¹] |
|---|---|---|---|---|---|---|---|---|---|---|
| 69c | H | H | H | H | H | H | n-C₃H₇ | H | CH | |
| 70c | H | H | H | H | H | H | n-C₃H₇ | CH₃ | CH | |
| 71c | H | H | H | H | H | H | n-C₄H₉ | H | CH | 2959, 1581, 1564, 1430, 778 |
| 72c | H | H | H | H | H | H | n-C₄H₉ | CH₃ | CH | |
| 73c | H | H | H | H | H | H | i-C₄H₉ | H | CH | 2958, 1581, 1564, 1430, 1044 |
| 74c | H | H | H | H | H | H | i-C₄H₉ | CH₃ | CH | |
| 75c | H | H | H | H | H | H | t-C₄H₉ | H | CH | |
| 76c | H | H | H | H | H | H | t-C₄H₉ | CH₃ | CH | |
| 77c | H | H | H | H | H | H | CH₂—CH=CH₂ | H | CH | |
| 78c | H | H | H | H | H | H | CH₂—CH=CH₂ | CH₃ | CH | |
| 79c | H | H | H | H | H | H | CH₂CH=CH—CH₃ | H | CH | |
| 80c | H | H | H | H | H | H | CH₂CH=CH—CH₃ | CH₃ | CH | |
| 81c | H | H | H | H | H | H | CH₂—C(CH₃)=CH₂ | H | CH | 1580, 1565, 1430, 1043, 778 |
| 82c | H | H | H | H | H | H | CH₂—C(CH₃)=CH₂ | CH₃ | CH | |
| 83c | H | H | H | H | H | H | CH₂—CH=CH—Cl | H | CH | 60–65° C. |
| 84c | H | H | H | H | H | H | CH₂—CH=CH—Cl | CH₃ | CH | |
| 85c | H | H | H | H | H | H | CH₂—C(Cl)=CH₂ | H | CH | |
| 86c | H | H | H | H | H | H | CH₂—C(Cl)=CH₂ | CH₃ | CH | |
| 87c | H | H | H | H | H | H | CH₂—C≡CH | H | CH | 110–115° C. |
| 88c | H | H | H | H | H | H | CH₂—C≡CH | CH₃ | CH | |
| 89c | H | H | H | H | H | H | (CH₂)₂—OCH₃ | H | CH | |
| 90c | H | H | H | H | H | H | (CH₂)₂—OCH₃ | CH₃ | CH | |
| 91c | H | H | H | H | H | H | (CH₂)₄—OCH₃ | H | CH | |
| 92c | H | H | H | H | H | H | (CH₂)₄—OCH₃ | CH₃ | CH | |
| 93c | H | H | H | H | H | H | cyclo-C₆H₁₁ | H | CH | |
| 94c | H | H | H | H | H | H | cyclo-C₆H₁₁ | CH₃ | CH | |
| 95c | H | H | H | H | H | H | C₆H₅ | H | CH | |
| 96c | H | H | H | H | H | H | C₆H₅ | CH₃ | CH | |
| 97c | H | H | H | H | H | H | C₆H₅CH₂ | H | CH | |
| 98c | H | H | H | H | H | H | C₆H₅CH₂ | CH₃ | CH | |
| 99c | H | H | H | H | H | H | 4-Cl—C₆H₄CH₂ | H | CH | 47° C. |
| 100c | H | H | H | H | H | H | 4-Cl—C₆H₄CH₂ | CH₃ | CH | |
| 101c | H | H | H | H | H | H | 4-F—C₆H₄CH₂ | H | CH | |
| 102c | H | H | H | H | H | H | 4-F—C₆H₄CH₂ | CH₃ | CH | |
| 103c | H | H | H | H | H | H | C₆H₅CH₂CH₂ | H | CH | |
| 104c | H | H | H | H | H | H | C₆H₅CH₂CH₂ | CH₃ | CH | |
| 105c | H | H | H | H | H | H | C₆H₅(CH₂)₄ | H | CH | 76 bis 78° C. |
| 106c | H | H | H | H | H | H | C₆H₅(CH₂)₄ | CH₃ | CH | |
| 107c | H | H | H | H | H | H | 4-Cl—C₆H₄(CH₂)₄ | H | CH | |
| 108c | H | H | H | H | H | H | 4-Cl—C₆H₄(CH₂)₄ | CH₃ | CH | |
| 109c | H | H | H | H | H | H | C₆H₅CH=CH—CH₂ | H | CH | |
| 110c | H | H | H | H | H | H | C₆H₅CH=CH—CH₂ | CH₃ | CH | |
| 111c | H | H | H | H | H | H | 4-Cl—C₆H₄CH=CH—CH₂ | H | CH | |
| 112c | H | H | H | H | H | H | 4-Cl—C₆H₄CH=CH—CH₂ | CH₃ | CH | |
| 113c | H | H | H | H | H | H | 4-Cl—C₆H₄CH=CH—(CH₂)₂ | H | CH | |
| 114c | H | H | H | H | H | H | 4-Cl—C₆H₄CH=CH—(CH₂)₂ | CH₃ | CH | |
| 115c | H | H | H | H | H | H | 4-Cl—C₆H₄CH₂—CH=CH—CH₂ | H | CH | |
| 116c | H | H | H | H | H | H | 4-Cl—C₆H₄CH₂—CH=CH—CH₂ | CH₃ | CH | |
| 117c | H | H | H | H | H | H | 2-F—C₆H₄OCH₂CH₂ | H | CH | 98–100° C. |
| 118c | H | H | H | H | H | H | 2-F—C₆H₄OCH₂CH₂ | CH₃ | CH | |
| 119c | H | H | H | H | H | H | 4-Cl—C₆H₄OCH(CH₃)CH₂ | H | CH | |
| 120c | H | H | H | H | H | H | 4-Cl—C₆H₄OCH(CH₃)CH₂ | CH₃ | CH | |
| 121c | H | H | H | H | H | H | C₆H₅O(CH₂)₄ | H | CH | |
| 122c | H | H | H | H | H | H | C₆H₅O(CH₂)₄ | CH₃ | CH | |
| 123c | H | H | H | H | H | H | cyclo-C₆H₁₁CH₂ | H | CH | |
| 124c | H | H | H | H | H | H | cyclo-C₆H₁₁CH₂ | CH₃ | CH | |
| 125c | CH₃ | H | H | H | CH₃ | H | H | H | N | 135° C. |
| 126c | CH₃ | H | H | H | CH₃ | H | H | CH₃ | N | |
| 127c | CH₃ | H | H | H | CH₃ | H | CH₃ | H | N | |
| 128c | CH₃ | H | H | H | CH₃ | H | CH₃ | CH₃ | N | |
| 129c | CH₃ | H | H | H | CH₃ | H | C₂H₅ | H | N | |
| 130c | CH₃ | H | H | H | CH₃ | H | C₂H₅ | CH₃ | N | |
| 131c | CH₃ | H | H | H | CH₃ | H | n-C₃H₇ | H | N | |
| 132c | CH₃ | H | H | H | CH₃ | H | n-C₃H₇ | CH₃ | N | |
| 133c | CH₃ | H | H | H | CH₃ | H | n-C₄H₉ | H | N | 2959, 1577, 1535, |

TABLE 1-continued

Ic

| Comp No. | R$^1$ | R$^2$ | R$^3$ | R$^4$ | R$^5$ | R$^6$ | R$^7$ | R$^{10}$ | X | mp./Ir (film) [cm$^{-1}$] |
|---|---|---|---|---|---|---|---|---|---|---|
| 134c | CH$_3$ | H | H | H | CH$_3$ | H | n-C$_4$H$_9$ | CH$_3$ | N | 1365, 1046 |
| 135c | CH$_3$ | H | H | H | CH$_3$ | H | i-C$_4$H$_9$ | H | N | |
| 136c | CH$_3$ | H | H | H | CH$_3$ | H | i-C$_4$H$_9$ | CH$_3$ | N | |
| 137c | CH$_3$ | H | H | H | CH$_3$ | H | t-C$_4$H$_9$ | H | N | |
| 138c | CH$_3$ | H | H | H | CH$_3$ | H | t-C$_4$H$_9$ | CH$_3$ | N | |
| 139c | CH$_3$ | H | H | H | CH$_3$ | H | CH$_2$—CH=CH$_2$ | H | N | |
| 140c | CH$_3$ | H | H | H | CH$_3$ | H | CH$_2$—CH=CH$_2$ | CH$_3$ | N | |
| 141c | CH$_3$ | H | H | H | CH$_3$ | H | CH$_2$CH=CH—CH$_3$ | H | N | |
| 142c | CH$_3$ | H | H | H | CH$_3$ | H | CH$_2$CH=CH—CH$_3$ | CH$_3$ | N | |
| 143c | CH$_3$ | H | H | H | CH$_3$ | H | CH$_2$—C(CH$_3$)=CH$_2$ | H | N | 1578, 1536, 1366, 1028, 779 |
| 144c | CH$_3$ | H | H | H | CH$_3$ | H | CH$_2$—C(CH$_3$)=CH$_2$ | CH$_3$ | N | |
| 145c | CH$_3$ | H | H | H | CH$_3$ | H | CH$_2$—CH=CH—Cl | H | N | |
| 146c | CH$_3$ | H | H | H | CH$_3$ | H | CH$_2$—CH=CH—Cl | CH$_3$ | N | |
| 147c | CH$_3$ | H | H | H | CH$_3$ | H | CH$_2$—C(Cl)=CH$_2$ | H | N | |
| 148c | CH$_3$ | H | H | H | CH$_3$ | H | CH$_2$—C(Cl)=CH$_2$ | CH$_3$ | N | |
| 149c | CH$_3$ | H | H | H | CH$_3$ | H | CH$_2$—C≡CH | H | N | 120° C. |
| 150c | CH$_3$ | H | H | H | CH$_3$ | H | CH$_2$—C≡CH | CH$_3$ | N | |
| 151c | CH$_3$ | H | H | H | CH$_3$ | H | (CH$_2$)$_2$—OCH$_3$ | H | N | |
| 152c | CH$_3$ | H | H | H | CH$_3$ | H | (CH$_2$)$_2$—OCH$_3$ | CH$_3$ | N | |
| 153c | CH$_3$ | H | H | H | CH$_3$ | H | (CH$_2$)$_4$—OCH$_3$ | H | N | |
| 154c | CH$_3$ | H | H | H | CH$_3$ | H | (CH$_2$)$_4$—OCH$_3$ | CH$_3$ | N | |
| 155c | CH$_3$ | H | H | H | CH$_3$ | H | cyclo-C$_6$H$_{11}$ | H | N | |
| 156c | CH$_3$ | H | H | H | CH$_3$ | H | cyclo-C$_6$H$_{11}$ | CH$_3$ | N | |
| 157c | CH$_3$ | H | H | H | CH$_3$ | H | C$_6$H$_5$ | H | N | |
| 158c | CH$_3$ | H | H | H | CH$_3$ | H | C$_6$H$_5$ | CH$_3$ | N | |
| 159c | CH$_3$ | H | H | H | CH$_3$ | H | C$_6$H$_5$CH$_2$ | H | N | 172 to 175° C. |
| 160c | CH$_3$ | H | H | H | CH$_3$ | H | C$_6$H$_5$CH$_2$ | CH$_3$ | N | |
| 161c | CH$_3$ | H | H | H | CH$_3$ | H | 4-Cl—C$_6$H$_4$CH$_2$ | H | N | |
| 162c | CH$_3$ | H | H | H | CH$_3$ | H | 4-Cl—C$_6$H$_4$CH$_2$ | CH$_3$ | N | |
| 163c | CH$_3$ | H | H | H | CH$_3$ | H | 4-F—C$_6$H$_4$CH$_2$ | H | N | |
| 164c | CH$_3$ | H | H | H | CH$_3$ | H | 4-F—C$_6$H$_4$CH$_2$ | CH$_3$ | N | |
| 165c | CH$_3$ | H | H | H | CH$_3$ | H | C$_6$H$_5$CH$_2$CH$_2$ | H | N | |
| 166c | CH$_3$ | H | H | H | CH$_3$ | H | C$_6$H$_5$CH$_2$CH$_2$ | CH$_3$ | N | |
| 167c | CH$_3$ | H | H | H | CH$_3$ | H | C$_6$H$_5$(CH$_2$)$_4$ | H | N | |
| 168c | CH$_3$ | H | H | H | CH$_3$ | H | C$_6$H$_5$(CH$_2$)$_4$ | CH$_3$ | N | |
| 169c | CH$_3$ | H | H | H | CH$_3$ | H | 4-Cl—C$_6$H$_4$(CH$_2$)$_4$ | H | N | |
| 170c | CH$_3$ | H | H | H | CH$_3$ | H | 4-Cl—C$_6$H$_4$(CH$_2$)$_4$ | CH$_3$ | N | |
| 171c | CH$_3$ | H | H | H | CH$_3$ | H | C$_6$H$_5$CH=CH—CH$_2$ | H | N | |
| 172c | CH$_3$ | H | H | H | CH$_3$ | H | C$_6$H$_5$CH=CH—CH$_2$ | CH$_3$ | N | |
| 173c | CH$_3$ | H | H | H | CH$_3$ | H | 4-Cl—C$_6$H$_4$CH=CH—CH$_2$ | H | N | |
| 174c | CH$_3$ | H | H | H | CH$_3$ | H | 4-Cl—C$_6$H$_4$CH=CH—CH$_2$ | CH$_3$ | N | |
| 175c | CH$_3$ | H | H | H | CH$_3$ | H | 4-Cl—C$_6$H$_4$CH=CH—(CH$_2$)$_2$ | H | N | |
| 176c | CH$_3$ | H | H | H | CH$_3$ | H | 4-Cl—C$_6$H$_4$CH=CH—(CH$_2$)$_2$ | CH$_3$ | N | |
| 177c | CH$_3$ | H | H | H | CH$_3$ | H | 4-Cl—C$_6$H$_4$CH$_2$—CH=CH—CH$_2$ | H | N | |
| 178c | CH$_3$ | H | H | H | CH$_3$ | H | 4-Cl—C$_6$H$_4$CH$_2$—CH=CH—CH$_2$ | CH$_3$ | N | |
| 179c | CH$_3$ | H | H | H | CH$_3$ | H | 2-F—C$_6$H$_4$OCH$_2$CH$_2$ | H | N | |
| 180c | CH$_3$ | H | H | H | CH$_3$ | H | 2-F—C$_6$H$_4$OCH$_2$CH$_2$ | CH$_3$ | N | |
| 181c | CH$_3$ | H | H | H | CH$_3$ | H | 4-Cl—C$_6$H$_4$OCH(CH$_3$)CH$_2$ | H | N | 1578, 1489, 1240, 1056, 825 |
| 182c | CH$_3$ | H | H | H | CH$_3$ | H | 4-Cl—C$_6$H$_4$OCH(CH$_3$)CH$_2$ | CH$_3$ | N | |
| 183c | CH$_3$ | H | H | H | CH$_3$ | H | C$_6$H$_5$O(CH$_2$)$_4$ | H | N | |
| 184c | CH$_3$ | H | H | H | CH$_3$ | H | C$_6$H$_5$O(CH$_2$)$_4$ | CH$_3$ | N | |
| 185c | CH$_3$ | H | H | H | CH$_3$ | H | cyclo-C$_6$H$_{11}$CH$_2$ | H | N | |
| 186c | CH$_3$ | H | H | H | CH$_3$ | H | cyclo-C$_6$H$_{11}$CH$_2$ | CH$_3$ | N | |
| 187c | CH$_3$ | H | H | H | H | H | H | H | CH | |
| 188c | CH$_3$ | H | H | H | H | H | n-C$_4$H$_9$ | CH$_3$ | CH | |
| 189c | CH$_3$ | CH$_3$ | H | H | H | H | CH$_2$CH=CH$_2$ | H | N | |
| 190c | H | H | C$_6$H$_5$ | H | CH$_3$ | H | C$_6$H$_5$CH$_2$ | H | N | |
| 191c | CH$_3$ | H | H | H | OCH$_3$ | H | H | CH$_3$ | N | 174–176° C. |
| 192c | CH$_3$ | H | H | H | OCH$_3$ | H | CH$_3$ | CH$_3$ | N | |
| 193c | CH$_3$ | H | H | H | OCH$_3$ | H | C$_6$H$_5$(CH$_2$)$_4$ | CH$_3$ | N | |
| 194c | CH$_3$ | H | H | H | OCH$_3$ | H | 4-Cl—C$_6$H$_4$CH=CH—(CH$_2$)$_2$ | CH$_3$ | N | |
| 195c | CH$_3$ | H | H | H | OCH$_3$ | H | n-C$_4$H$_9$ | CH$_3$ | N | 1574, 1542, 1455, 1382, 1044 |
| 196c | C$_6$H$_5$ | H | H | H | CH$_3$ | H | H | H | N | |
| 197c | C$_6$H$_5$ | H | H | H | H | H | n-C$_4$H$_9$ | H | N | |

TABLE 1-continued

Ic

| Comp No. | R¹ | R² | R³ | R⁴ | R⁵ | R⁶ | R⁷ | R¹⁰ | X | mp./Ir (film) [cm⁻¹] |
|---|---|---|---|---|---|---|---|---|---|---|
| 198c | $C_6H_5$ | H | H | H | $OCH_3$ | H | $C_6H_5CH_2$ | $CH_3$ | N | |
| 199c | $C_6H_5$ | H | H | H | $CH_3$ | H | $i-C_4H_9$ | H | N | |
| 200c | $C_6H_5$ | H | H | H | H | H | $4-Cl-C_6H_4(CH_2)_4$ | H | N | |
| 201c | $C_6H_5$ | H | H | H | $OCH_3$ | H | $CH_2C\equiv CH$ | $CH_3$ | N | |
| 202c | $C_6H_5$ | H | H | H | $CH_3$ | H | $C_6H_5O(CH_2)_4$ | H | N | |
| 203c | $C_6H_5$ | H | H | H | H | H | cyclo-$C_6H_{11}$ | H | N | |
| 204c | $C_6H_5$ | H | H | H | $OCH_3$ | H | cyclo-$C_6H_{11}CH_2$ | $CH_3$ | N | |
| 205c | $n-C_3H_7$ | H | H | H | $CH_3$ | H | $CH_3$ | H | N | |
| 206c | $C_6H_5CH_2$ | H | H | H | $OCH_3$ | H | $CH_2CH=CH-Cl$ | $CH_3$ | N | |
| 207c | H | H | H | H | H | H | $4-Cl-C_6H_4(CH_2)_6$ | H | N | 30–31° C. |
| 208c | $CH_3$ | H | H | H | H | H | $n-C_4H_9$ | H | N | 1568, 1549, 1438, 1386, 1031 |
| 209c | $CH_3$ | H | H | H | H | H | $CH_2-C\equiv CH$ | H | N | 94–95° C. |
| 210c | $CH_3$ | H | H | H | H | H | $4-Cl-C_6H_4CH(CH_3)$ | H | N | 1568, 1549, 1386, 1014, 974 |
| 211c | $CH_3$ | H | H | H | H | H | $C_6H_5(CH_2)_4$ | H | N | 1567, 1549, 1438, 1386, 1043 |
| 212c | $CH_3$ | H | H | H | H | H | $4-Cl-C_6H_4OCH(CH_3)CH_2$ | H | N | 1568, 1489, 1386, 1240, 1053 |
| 213c | $CH_3$ | H | H | H | $OCH_3$ | H | $4-Cl-C_6-C_4CH_2$ | $CH_3$ | N | 140° C. |
| 214c | $CH_3$ | H | H | H | $OCH_3$ | H | $4-Cl-C_6H_4(CH_2)_4$ | $CH_3$ | N | 1574, 1542, 1492, 1382, 1045 |
| 215c | $C_6H_5$ | H | H | H | H | H | $C_6H_5CH_2$ | H | CH | 99° C. |
| 216c | $C_6H_5$ | H | H | H | H | H | $C_6H_5(CH_2)_4$ | H | CH | 63° C. |
| 217c | $C_6H_5$ | H | H | H | H | H | $4-Cl-C_6H_4CH=CH-(CH_2)_2$ | H | CH | 104° C. |
| 218c | $C_6H_5$ | H | H | H | H | H | $4-Cl-C_6H_4OCH(CH_3)CH_2$ | H | CH | 1566, 1489, 1439, 1240, 763 |
| 219c | $C_6H_5$ | H | H | H | H | H | $CH_2-C\equiv CH$ | H | CH | 99° C. |
| 220c | $C_6H_5$ | H | H | H | H | H | $CH_3$ | H | CH | 89° C. |
| 221c | $C_6H_5$ | H | H | H | H | H | $n-C_4H_9$ | H | CH | 1566, 1439, 1070, 805, 763 |

TABLE 2

Id

| Comp No. | R¹ | R² | R³ | R⁴ | R⁵ | R⁶ | R⁷ | R¹¹ | X | mp./Ir (film) [cm⁻¹] |
|---|---|---|---|---|---|---|---|---|---|---|
| 1d | H | H | H | H | H | H | $CH_3$ | H | N | |
| 2d | H | H | H | H | H | H | $n-C_4H_9$ | H | N | |
| 3d | H | H | H | H | $CH_3$ | H | $CH_2-CH=CH_2$ | H | N | |
| 4d | H | H | H | H | $CH_3$ | Cl | cyclo-$C_6H_{11}$ | H | N | |
| 5d | H | H | H | H | $n-C_3H_7$ | H | $C_6H_5CH_2$ | H | N | |
| 6d | H | H | H | H | $n-C_3H_7$ | H | H | H | N | |
| 7d | H | H | H | H | cyclo-$C_5H_9$ | H | $4-Cl-C_6H_4CH_2$ | H | N | |
| 8d | H | H | H | H | $C_6H_5$ | H | $n-C_3H_7$ | H | N | |
| 9d | H | H | $C_6H_5$ | H | $CH_3$ | Cl | H | H | N | |
| 10d | $CH_3$ | H | H | H | H | H | $CH_3$ | H | N | |
| 11d | $CH_3$ | H | H | H | $CH_3$ | H | H | H | N | |
| 12d | $CH_3$ | H | H | H | $CH_3$ | H | $n-C_4H_9$ | H | N | |
| 13d | $CH_3$ | H | H | H | $n-C_3H_7$ | H | $CH_2-CH=CH_2$ | H | N | |
| 14d | $CH_3$ | H | H | H | $n-C_3H_7$ | H | $CH_2C\equiv CH$ | H | N | |
| 15d | $CH_3$ | H | H | H | cyclo-$C_5H_9$ | H | $C_6H_5$ | H | N | |
| 16d | $CH_3$ | H | H | H | $C_6H_5$ | H | $CH_3$ | H | N | |
| 17d | $CH_3$ | $CH_3$ | H | H | $C_6H_5CH_2$ | H | $CH_2C(Cl)=CH_2$ | H | N | |
| 18d | $CH_3$ | H | H | H | $CH_3$ | Cl | H | H | N | |

TABLE 2-continued

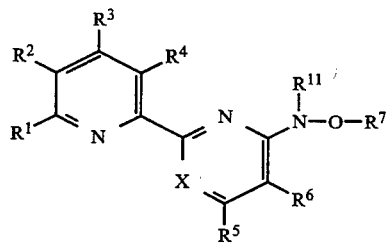

Id

| Comp No. | R$^1$ | R$^2$ | R$^3$ | R$^4$ | R$^5$ | R$^6$ | R$^7$ | R$^{11}$ | X | mp./Ir (film) [cm$^{-1}$] |
|---|---|---|---|---|---|---|---|---|---|---|
| 19d | CH$_3$ | H | H | H | CH$_3$ | Cl | CH$_3$ | H | N | |
| 20d | CH$_3$ | H | H | H | CH$_3$ | Cl | n-C$_4$H$_9$ | H | N | 62° C. |
| 21d | CH$_3$ | H | H | H | CH$_3$ | Cl | CH$_2$—CH=CH$_2$ | H | N | |
| 22d | CH$_3$ | H | H | H | CH$_3$ | Cl | CH$_2$—C(CH$_3$)=CH$_2$ | H | N | 121–124° C. |
| 23d | CH$_3$ | H | H | H | CH$_3$ | Cl | CH$_2$—CH=CH—CH$_3$ | H | N | 105° C. |
| 24d | CH$_3$ | H | H | H | CH$_3$ | Cl | CH$_2$—CH=CH—Cl | H | N | |
| 25d | CH$_3$ | H | H | H | CH$_3$ | Cl | CH$_2$—C(Cl)=CH$_2$ | H | N | |
| 26d | CH$_3$ | H | H | H | CH$_3$ | Cl | CH$_2$—C≡CH | H | N | |
| 27d | CH$_3$ | H | H | H | CH$_3$ | Cl | (CH$_2$)$_2$OCH$_3$ | H | N | |
| 28d | CH$_3$ | H | H | H | CH$_3$ | Cl | (CH$_2$)$_4$OCH$_3$ | H | N | |
| 29d | CH$_3$ | H | H | H | CH$_3$ | Cl | cyclo-C$_6$H$_{11}$ | H | N | |
| 30d | CH$_3$ | H | H | H | CH$_3$ | Cl | cyclo-C$_6$H$_{11}$CH$_2$ | H | N | |
| 31d | CH$_3$ | H | H | H | CH$_3$ | Cl | C$_6$H$_5$ | H | N | |
| 32d | CH$_3$ | H | H | H | CH$_3$ | Cl | C$_6$H$_5$CH$_2$ | H | N | |
| 33d | CH$_3$ | H | H | H | CH$_3$ | Cl | 4-Cl—C$_6$H$_4$CH$_2$ | H | N | 150° C. |
| 34d | CH$_3$ | H | H | H | CH$_3$ | Cl | C$_6$H$_5$(CH$_2$)$_4$ | H | N | |
| 35d | CH$_3$ | H | H | H | CH$_3$ | Cl | 4-Cl—C$_6$H$_4$(CH$_2$)$_4$ | H | N | 1630, 1606, 1590, 1491, 1438 |
| 36d | CH$_3$ | H | H | H | CH$_3$ | Cl | 4-Cl—C$_6$H$_4$CH=CH—(CH$_2$)$_2$ | H | N | 92–94° C. |
| 37d | CH$_3$ | H | H | H | CH$_3$ | Cl | 4-Cl—C$_6$H$_4$OCH(CH$_3$)CH$_2$ | H | N | 72–74° C. |
| 38d | CH$_3$ | H | H | H | CH$_3$ | Cl | C$_6$H$_5$O(CH$_2$)$_4$ | H | N | |
| 39d | C$_6$H$_5$ | H | H | H | n-C$_3$H$_7$ | H | CH$_3$ | N | H | |
| 40d | C$_6$H$_5$ | H | H | H | C$_6$H$_5$ | H | H | H | N | |
| 41d | C$_6$H$_5$ | H | H | H | CH$_3$ | Cl | C$_6$H$_5$CH$_2$ | H | N | |
| 42d | C$_6$H$_5$ | H | H | H | CH$_3$ | Br | n-C$_4$H$_9$ | H | N | |
| 43d | C$_6$H$_5$ | H | H | H | CH$_3$ | Cl | CH$_3$ | CH$_3$ | N | |
| 44d | C$_6$H$_5$ | H | H | H | CH$_3$ | Cl | cyclo-C$_6$H$_{11}$ | CH$_3$ | N | |
| 45d | CH$_3$ | H | H | H | CH$_3$ | Cl | CH$_3$ | CH$_3$ | N | 1549, 1433, 1384, 1058, 776 |
| 46d | H | H | H | H | H | H | H | H | CH$_3$ | |
| 47d | H | H | H | H | H | H | CH$_3$ | H | CH$_3$ | |
| 48d | H | H | H | H | H | H | n-C$_4$H$_9$ | H | CH$_3$ | |
| 49d | H | H | H | H | H | H | CH$_2$—CH=CH$_2$ | H | CH$_3$ | |
| 50d | H | H | H | H | H | H | CH$_2$—CH=CH—Cl | H | CH$_3$ | |
| 51d | H | H | H | H | H | H | CH$_2$—C≡CH | H | CH$_3$ | |
| 52d | H | H | H | H | H | H | (CH$_2$)$_2$OCH$_3$ | H | CH$_3$ | |
| 53d | H | H | H | H | H | H | cyclo-C$_6$H$_{11}$ | H | CH$_3$ | |
| 54d | H | H | H | H | H | H | cyclo-C$_6$H$_{11}$CH$_2$ | H | CH$_3$ | |
| 55d | H | H | H | H | H | H | C$_6$H$_5$ | H | CH$_3$ | |
| 56d | H | H | H | H | H | H | C$_6$H$_5$CH$_2$ | H | CH$_3$ | |
| 57d | H | H | H | H | H | H | 4-Cl—C$_6$H$_4$CH$_2$ | H | CH$_3$ | |
| 58d | H | H | H | H | H | H | 4-Cl—C$_6$H$_4$(CH$_2$)$_4$ | H | CH$_3$ | |
| 59d | H | H | H | H | H | H | 4-Cl—C$_6$H$_4$CH=CH—(CH$_2$)$_2$ | H | CH$_3$ | |
| 60d | H | H | H | H | H | H | 4-Cl—C$_6$H$_4$OCH(CH$_3$)CH$_2$ | H | CH$_3$ | |
| 61d | H | H | H | H | H | H | C$_6$H$_5$O(CH$_2$)$_4$ | H | CH$_3$ | |
| 62d | CH$_3$ | H | H | H | H | H | n-C$_4$H$_9$ | H | CH$_3$ | |
| 63d | CH$_3$ | CH$_3$ | H | H | H | H | 4-Cl—C$_6$H$_4$CH$_2$ | H | CH$_3$ | |
| 64d | C$_6$H$_5$ | H | H | H | H | H | CH$_2$—C(CH$_3$)=CH$_2$ | H | CH$_3$ | |
| 65d | H | H | C$_6$H$_5$ | H | H | H | C$_6$H$_5$O(CH$_2$)$_4$ | H | CH$_3$ | |
| 66d | CH$_3$ | H | H | H | CH$_3$ | Cl | i-C$_4$H$_9$ | H | N | 108–110° C. |
| 67d | CH$_3$ | H | H | H | (CH$_2$)$_3$ | | CH$_2$CH=CH—CH$_3$ | H | N | 102–104° C. |
| 68d | CH$_3$ | H | H | H | (CH$_2$)$_3$ | | 4-Cl—C$_6$H$_4$CH$_2$ | H | N | 140–142° C. |
| 69d | CH$_3$ | H | H | H | CH$_3$ | Cl | n-C$_5$H$_{11}$ | H | N | 41–44° C. |

TABLE 3

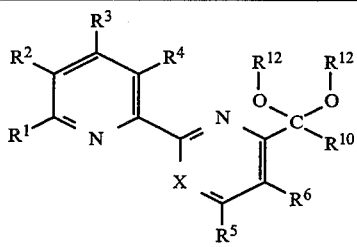

V

| Comp No. | $R^1$ | $R^2$ | $R^3$ | $R^4$ | $R^5$ | $R^6$ | $R^{10}$ | $R^{12}$ | X | mp./Ir (film) [cm$^{-1}$] |
|---|---|---|---|---|---|---|---|---|---|---|
| 1.3 | H | H | H | H | H | H | H | $CH_3$ | N | 42° C. |
| 2.3 | H | H | H | H | H | H | H | $CH_3CH_2$ | N | |
| 3.3 | H | H | H | H | H | H | $CH_3$ | $(CH_2)_2$ | N | |
| 4.3 | $CH_3$ | H | H | H | $CH_3$ | H | H | $CH_3CH_2$ | N | 2975, 1581, 1372, 1112, 1062 |
| 5.3 | $CH_3$ | H | H | H | $CH_3$ | H | $CH_3$ | $(CH_2)_2$ | N | |
| 6.3 | $CH_3$ | $CH_3$ | H | H | H | H | H | $CH_3$ | N | |
| 7.3 | H | H | $C_6H_5$ | H | $CH_3$ | H | H | $CH_3CH_2$ | N | |
| 8.3 | $CH_3$ | H | H | H | $OCH_3$ | H | $CH_3$ | $(CH_2)_2$ | N | 105–107° C. |
| 9.3 | $C_6H_5$ | H | H | H | H | H | H | $CH_3$ | N | |
| 10.3 | $C_6H_5$ | H | H | H | $CH_3$ | H | H | $CH_3CH_2$ | N | |
| 11.3 | $C_6H_5$ | H | H | H | $OCH_3$ | H | H | $CH_3$ | N | |
| 12.3 | n-$C_3H_7$ | H | H | H | $CH_3$ | H | H | $CH_3CH_2$ | N | |
| 13.3 | $C_6H_5CH_2$ | H | H | H | $OCH_3$ | H | $CH_3$ | $(CH_2)_2$ | N | |
| 14.3 | $CH_3$ | H | H | H | OH | H | $CH_3$ | $(CH_2)_2$ | N | 149–151° C. |
| 15.3 | $CH_3$ | H | H | H | Cl | H | $CH_3$ | $(CH_2)_2$ | N | 146–149° C. |
| 16.3 | $CH_3$ | H | H | H | H | H | H | $CH_3$ | N | 1572, 1558, 1431, 1112, 1067 |

TABLE 4

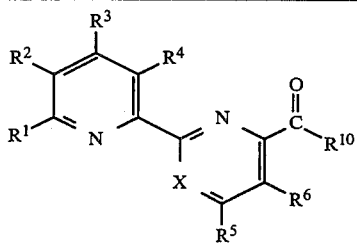

II

| Comp No. | $R^1$ | $R^2$ | $R^3$ | $R^4$ | $R^5$ | $R^6$ | $R^{10}$ | X | mp./Ir (film) [cm$^{-1}$] |
|---|---|---|---|---|---|---|---|---|---|
| 1.4 | H | H | H | H | H | H | H | N | 110–112° C. |
| 2.4 | H | H | H | H | H | H | $CH_3$ | N | |
| 3.4 | $CH_3$ | H | H | H | $CH_3$ | H | H | N | Harz |
| 4.4 | $CH_3$ | H | H | H | $CH_3$ | H | $CH_3$ | N | |
| 5.4 | $CH_3$ | $CH_3$ | H | H | H | H | H | N | |
| 6.4 | H | H | $C_6H_5$ | H | $CH_3$ | H | H | N | |
| 7.4 | $CH_3$ | H | H | H | $OCH_3$ | H | $CH_3$ | N | 1702, 1576, 1554, 1387, 1364 |
| 8.4 | $C_6H_5$ | H | H | H | H | H | H | N | |
| 9.4 | $C_6H_5$ | H | H | H | $CH_3$ | H | H | N | |
| 10.4 | $C_6H_5$ | H | H | H | $OCH_3$ | H | H | N | |
| 11.4 | n-$C_3H_7$ | H | H | H | $CH_3$ | H | H | N | |
| 12.4 | $C_6H_5CH_2$ | H | H | H | $OCH_3$ | H | $CH_3$ | N | |
| 13.4 | $CH_3$ | H | H | H | H | H | H | CH | |
| 14.4 | $CH_3$ | H | H | H | H | H | $CH_3$ | CH | |
| 15.4 | $CH_3$ | $CH_3$ | H | H | H | H | H | CH | |
| 16.4 | $C_6H_5$ | H | H | H | H | H | H | CH | 93° C. |
| 17.4 | H | H | $C_6H_5$ | H | H | H | H | CH | |
| 18.4 | $CH_3$ | H | H | H | H | H | H | N | 125° C. |

The novel compounds are suitable as fungicides, insecticides, nematocides and for regulating the growth of plants.

The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingedients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl poiyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of such formulations are given below.

I. A solution of 90 parts by weight of compound 1c and 10 parts by weight of N-methyl-α-pyrrolidone, which is suitable for application in the form of very fine drops.

II. A mixture of 20 parts by weight of compound no. 3c, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, a dispersion is obtained.

III. An aqueous dispersion of 20 parts by weight of compound 20d, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound 63c, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound 65c, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound 71c and 97 parts by weight of particulate kaolin. The dust contains 3 wt % of the active ingredient.

VII. An intimate mixture of 30 parts by weight of compound 73c, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound 133c, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound 159c, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a remarkably high systemic mobility and action after application to the soil and particularly to foliage.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the seeds, plants, materials or soil to be protected against fungus attack with a fungicidally effective amount of the active ingredients.

The compounds may be applied before or after infection of the materials, plants or seeds by the fungi.

The compounds I are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,

*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), for example against Paecilomyces variotii.

The fungicidal agents generally contain from 0.1 to 95, and preferably from 0.5 to 90, wt % of active ingredient.

The application rates depend on the type of effect desired, but are generally from 0.02 to 3 kg of active ingredient per hectare.

When the active ingredients are used for treating seed, application rates of from 0,001 to 50, and preferably from 0.01 to 10, g per kg of seed are generally required.

When the agents according to the invention are used as fungicides, they may be employed together with other active ingredients, e.g., herbicides, insecticides, growth regulators, other fungicides and fertilizers.

Use Example 1

Action on *Pyricularia oryzae* (protective)

Leaves of pot-grown rice seedlings of the "Tai-Nong 67" variety were sprayed to runoff with aqueous emulsions containing (dry basis) 80% of active ingredient and 20% of emulsifier, and inoculated 24 hours later with an aqueous spore suspension of Pyricularia oryzae. The plants were then set up in climatic cabinets at 22° to 24° C. and 95 to 99% relative humidity. The extent of fungus attack was assessed after 6 days.

The results of the experiment show that compounds 3c, 63c, 65c, 71c, 133c, 159c and 20d, when applied as aqueous spray liquors containing 250 ppm of active ingredient, have a good fungicidal action (90%).

We claim:

1. A substituted pyridine compound of the formula I

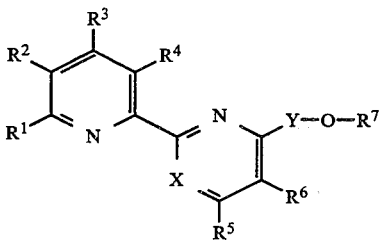

where
$R^1$ is hydrogen, $C_1$–$C_6$-alkyl, $C_1$–$C_4$-alkoxy-$C_1$–$C_4$-alkyl, $C_1$–$C_4$-alkylthio-$C_1$–$C_4$-alkyl, $C_2$–$C_6$-alkenyl, $C_2$–$C_6$-alkynyl, $C_3$–$C_7$-cycloalkyl, where the cycloalkyl radical may be monosubstituted, disubstituted or trisubstituted by $C_1$–$C_4$-alkyl, or halogen, phenyl, phenoxy-$C_1$–$C_4$-alkyl, phenylmercapto-$C_1$–$C_4$-alkyl, phenyl-$C_1$–$C_4$-alkyl, phenoxy or phenylmercapto, where the six last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy;

$R^2$, $R^3$ and $R^4$ independently of one another are each hydrogen, $C_1$–$C_6$-alkyl or phenyl where the phenyl radical may be monosubstituted, disubstituted or trisubstituted by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy;

$R^5$ is hydrogen, $C_1$–$C_6$-alkyl, $C_3$–$C_7$-cycloalkyl, $C_3$–$C_7$-cycloalkyl-$C_1$–$C_4$-alkyl, where the two last mentioned radicals may be monosubstituted, disubstituted or trisubstituted in the cycloalkyl moiety by $C_1$–$C_4$-alkyl, or $C_1$–$C_4$-haloalkyl, $C_1$–$C_4$-alkoxy, $C_1$–$C_4$-alkylthio, $C_1$–$C_4$-alkoxy-$C_1$–$C_4$-alkyl, $R^8R^9N$—, $C_1$–$C_4$-alkylthio-$C_1$–$C_4$-alkyl, hydroxyl, halogen, $C_2$–$C_6$-alkenyl, $C_2$–$C_6$-alkynyl, $C_3$–$C_6$-alkenyloxy, $C_3$–$C_6$-alkynyloxy, phenyl, phenoxy, phenyl-$C_1$–$C_4$-alkyl, phenoxy-$C_1$–$C_4$-alkyl, phenylmercapto-$C_1$–$C_4$-alkyl or phenylmercapto, where the six last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy;

$R^6$ is hydrogen, $C_1$–$C_4$-alkyl, $C_1$–$C_4$-alkoxy, $C_1$–$C_4$-alkoxycarbonyl, halogen or phenyl, where the phenyl radical may be monosubstituted, disubstituted or trisubstituted by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, or $R^5$ and $R^6$ together form a polymethylene chain of the formula —$(CH_2)_m$— in which m is 3 or 4;

$R^7$ is hydrogen, $C_1$–$C_{12}$-alkyl, $C_3$–$C_{12}$-alkenyl, $C_3$–$C_8$-alkynyl, where the three last-mentioned groups may be monosubstituted, disubstituted or trisubstituted by halogen, or $C_1$–$C_6$-alkoxy-$C_2$–$C_{10}$-alkyl, monocyclic or polycyclic $C_3$–$C_{10}$-cycloalkyl or $C_3$–$C_{10}$-cycloalkylmethyl, where these rings may be monosubstituted, disubstituted or trisubstituted by $C_1$–$C_4$-alkyl or monosubstituted by phenyl, or monocyclic or polycyclic $C_5$–$C_{10}$-cycloalkenyl or $C_5$–$C_{10}$-cycloalkenylmethyl, where these rings may be monosubstituted, disubstituted or trisubstituted by $C_1$–$C_4$-alkyl or monosubstituted by phenyl, or phenyl or phenyl-$C_1$–$C_6$-alkyl, phenyl-$C_3$–$C_6$-alkenyl or phenoxy-$C_2$–$C_6$-alkyl, where the four last-mentioned radicals may be monosubstituted, disubstituted or trisubstituted in the phenyl moiety by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^8$ and $R^9$ independently of one another are each hydrogen, $C_1$–$C_6$-alkyl, $C_3$–$C_6$-alkenyl, $C_3$–$C_6$-alkynyl, $C_3$–$C_7$-cycloalkyl, where the cycloalkyl radical may be monosubstituted, disubstituted or trisubstituted by $C_1$–$C_4$-alkyl, or phenyl or phenyl-$C_1$–$C_4$-alkyl, where the two last-mentioned radicals may be monosubstituted, disubstituted or trisubstituted in the phenyl moiety by halogen, nitro, cyano, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy, or the two radicals $R^8$ and $R^9$, together with the nitrogen atom to which they are bonded, form an unsubstituted or monosubstituted, disubstituted, trisubstituted or tetrasubstituted 5- to 7-membered, saturated or unsaturated heterocyclic structure having 1 to 3 identical or different heteroatoms selected from the group consisting of nitrogen, oxygen and sulfur, and the substituent $C_1$–$C_4$-alkyl;

X is CH or N;

Y is

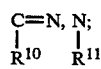

$R^{10}$ is hydrogen or $C_1$–$C_6$-alkyl and $R^{11}$ is hydrogen, $C_1$–$C_6$-alkyl or $C_3$–$C_8$-cycloalkyl, where the cycloalkyl radical may be monosubstituted, disubstituted or trisubstituted by $C_1$–$C_4$-alkyl or monosubstituted by phenyl, or phenyl or phenyl-$C_1$–$C_4$-alkyl, where the two last-mentioned radicals may be monosubstituted, disubstituted or trisubstituted in the phenyl moiety by halogen, $C_1$–$C_4$-alkyl, $C_1$–$C_4$-alkoxy or $C_1$–$C_4$-haloalkyl, or its plant-tolerated acid addition salts or metal salt complexes, with the exception of the compounds E-6-formyloximino-4-methoxy-2,2'-bipyridine, Z-6-formyloximino-4-methoxy-2,2'-bipyridine and 6-formyl-O-methyloximino-4-methoxy-2,2'-bipyridine.

2. A substituted pyridine compound of the formula I as claimed in claim 1, wherein $R^1$ is hydrogen, $C_1$–$C_6$-alkyl, $C_1$–$C_3$-alkoxy-$C_1$- or $C_2$-alkyl, phenyl, phenyl-$C_1$- or $C_2$-alkyl or phenoxy-$C_1$- or $C_2$-alkyl, where the three last-mentioned radicals may be monosubstituted, disubstituted or trisubstituted in the phenyl moiety by halogen or by $C_1$–$C_4$-alkyl, $R^2$ and $R^3$ independently of one another are each hydrogen, $C_1$–$C_3$-alkyl or phenyl, where the phenyl radical may be monosubstituted, disubstituted or trisubstituted by halogen or by $C_1$–$C_4$-alkyl, $R^4$ is hydrogen, $R^5$ is hydrogen, $C_1$–$C_6$-alkyl, $C_3$–$C_6$-cycloalkyl, $C_5$- or $C_6$-cycloalkyl-$C_1$–$C_3$-alkyl, halogen, phenyl or phenyl-$C_1$- or $C_2$-alkyl, where the two last-mentioned radicals may be unsubstituted or monosubstituted, disubstituted or trisubstituted in the phenyl moiety by halogen, $C_1$–$C_4$-alkyl or $C_1$–$C_4$-alkoxy, or $R^5$ is $C_1$–$C_3$-haloalkyl, $C_1$–$C_4$-alkoxy or $C_1$–$C_4$-alkylthio, $R^6$ is hydrogen, $C_1$–$C_4$-alkyl, halogen, phenyl or $C_1$–$C_3$-alkoxy, or $R^5$ and $R^6$ together form a polyethylene chain of the formula —$(CH_2)_m$— in which m is 3 or 4, $R^7$ is hydrogen, $C_1$–$C_6$-alkyl, $C_3$–$C_6$-alkenyl or $C_3$–$C_6$-alkynyl, where the three last-mentioned groups may be monosubstituted, disubstituted or trisubstituted by halogen, or $C_1$–$C_3$-alkoxy-$C_2$–$C_6$-alkyl, monocyclic or polycyclic $C_3$–$C_{10}$-cycloalkyl or $C_3$–$C_{10}$-cycloalkylmethyl, where these rings may be monosubstituted or disubstituted by $C_1$–$C_4$-alkyl or monosubstituted by phenyl, monocyclic or polycyclic $C_5$–$C_{10}$-cycloalkenyl or $C_5$–$C_{10}$-cycloalkenylmethyl, where these rings may be monosubstituted or disubstituted by $C_1$–$C_4$-alkyl or monosubstituted by phenyl, phenyl, phenyl-$C_1$–$C_6$-alkyl, phenyl-$C_3$–$C_6$-alkenyl or phenoxy-$C_2$–$C_6$-alkyl, where the four last-mentioned radicals may be monosubstituted, disubstituted or trisubstituted in the phenyl moiety by halogen, $C_1$–$C_4$-alkyl, $C_1$–$C_3$-haloalkyl or $C_1$–$C_4$-alkoxy, X is CH or N, Y is

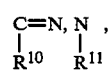

$R^{10}$ is hydrogen or $C_1$–$C_4$-alkyl and $R^{11}$ is hydrogen, $C_1$–$C_4$-alkyl or $C_3$–$C_8$-cycloalkyl, where the cycloalkyl radical may be monosubstituted or disubstituted ed by $C_1$–$C_4$-alkyl or monosubstituted by phenyl, or $R^{11}$ is phenyl, phenyl -$C_1$- or $C_2$-alkyl, where the two last-mentioned radicals may be monosubstituted, disubstituted or trisubstituted in the phenyl moiety by halogen, $C_1$–$C_4$-alkyl, $C_1$–$C_4$-alkoxy or $C_1$–$C_3$-haloalkyl, or its plant-tolerated acid addition salts or metal salt complexes.

3. A fungicide composition containing at least one substituted pyridine compound of the formula I or its plant-tolerated acid addition salt or metal salt complex as claimed in claim 1 and a liquid or solid carrier.

4. A method for controlling fungi, wherein a fungicidal amount of a substituted pyridine compound of the formula I or of its plant-tolerated acid addition salts or metal salt complexes as claimed in claim 1 is allowed to act on fungi, plants threatened by fungal attack, their habitat or the seed of the threatened plants.

* * * * *